United States Patent
Nishioka et al.

(10) Patent No.: US 12,414,702 B2
(45) Date of Patent: Sep. 16, 2025

(54) MEDICAL INFORMATION PROCESSING SYSTEM AND MEDICAL INFORMATION PROCESSING METHOD

(71) Applicant: CANON MEDICAL SYSTEMS CORPORATION, Otawara (JP)

(72) Inventors: Takahiko Nishioka, Otawara (JP); Hideaki Ishii, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1086 days.

(21) Appl. No.: 16/598,294

(22) Filed: Oct. 10, 2019

(65) Prior Publication Data

US 2020/0113450 A1 Apr. 16, 2020

(30) Foreign Application Priority Data

Oct. 10, 2018 (JP) ................. 2018-191548

(51) Int. Cl.
| | |
|---|---|
| *G01N 33/48* | (2006.01) |
| *A61B 5/00* | (2006.01) |
| *A61B 5/02* | (2006.01) |
| *A61B 5/026* | (2006.01) |
| *A61B 6/00* | (2006.01) |
| *A61B 6/46* | (2024.01) |
| *A61B 6/50* | (2024.01) |
| *G06T 7/00* | (2017.01) |
| *G16H 10/60* | (2018.01) |
| *G16H 50/30* | (2018.01) |
| *A61B 6/03* | (2006.01) |

(52) U.S. Cl.
CPC .......... *A61B 5/026* (2013.01); *A61B 5/02007* (2013.01); *A61B 5/02028* (2013.01); *A61B 5/7278* (2013.01); *A61B 5/743* (2013.01); *A61B 6/463* (2013.01); *A61B 6/486* (2013.01); *A61B 6/503* (2013.01); *A61B 6/504* (2013.01); *A61B 6/507* (2013.01); *A61B 6/5217* (2013.01); *G06T 7/0012* (2013.01); *G16H 10/60* (2018.01); *G16H 50/30* (2018.01); *A61B 6/032* (2013.01); *A61B 6/466* (2013.01); *A61B 6/469* (2013.01); *A61B 6/563* (2013.01); *G06T 2207/10081* (2013.01); *G06T 2207/20104* (2013.01); *G06T 2207/30101* (2013.01); *G06T 2207/30172* (2013.01)

(58) Field of Classification Search
None
See application file for complete search history.

(56) References Cited

FOREIGN PATENT DOCUMENTS

JP 2015-039448 A 3/2015

OTHER PUBLICATIONS

Roberts, W. T., J. J. Bax, and L. C. Davies. "Cardiac CT and CT coronary angiography: technology and application." Heart 94.6 (2008): 781-792.*
Gupta, Ankur, et al. "Integrated noninvasive physiological assessment of coronary circulatory function and impact on cardiovascular mortality in patients with stable coronary artery disease." Circulation 136.24 (2017): 2325-2336.*
Gaur, Sara, et al. "Rationale and design of the HeartFlowNXT (HeartFlow analysis of coronary blood flow using CT angiography: NeXt sTeps) study." Journal of cardiovascular computed tomography 7.5 (2013): 279-288.*
Kaul, Sanjiv, and Ananda R. Jayaweera. "Myocardial capillaries and coronary flow reserve." Journal of the American College of Cardiology 52.17 (2008): 1399-1401.*

* cited by examiner

*Primary Examiner* — Anna Skibinsky
(74) *Attorney, Agent, or Firm* — Oblon, McClelland, Maier &Neustadt, L.L.P.

(57) ABSTRACT

A medical information processing system according to an embodiment includes processing circuitry. The processing circuitry acquires a blood-vessel blood flow index in a coronary artery and a myocardial blood flow index in a myocardial region to which the coronary artery supplies blood. The processing circuitry calculates an index indicating a capability to supply the blood to the myocardial region by combining the blood-vessel blood flow index and the myocardial blood flow index.

22 Claims, 15 Drawing Sheets

FIG.17

|   | FFR | MBF | CAPILLARY RESISTANCE INDEX | RECOMMENDED TREATMENT |
|---|---|---|---|---|
| 1 | ↓ | ↓ | ↑ | CATHETER TREATMENT |
| 2 | ↑ | ↓ | ↓ | DRUG TREATMENT |
| 3 | ↓ | ↑ | ↑ | TREATMENT IS NOT NEEDED |
| 4 | ↓ | ↓ | ↓ | CATHETER TREATMENT/ DRUG TREATMENT |

MEDICAL INFORMATION PROCESSING SYSTEM AND MEDICAL INFORMATION PROCESSING METHOD

CROSS-REFERENCE TO RELATED APPLICATIONS

This application is based upon and claims the benefit of priority from Japanese Patent Application No. 2018-191548, filed on Oct. 10, 2018; the entire contents of which are incorporated herein by reference.

FIELD

Embodiments described herein relate generally to a medical information processing system and a medical information processing method.

BACKGROUND

Conventionally, it has been known that when evaluating a state of myocardial ischemia, it is important to evaluate capillary vascular resistance (microcirculation resistance) in a myocardium as well a blood flow volume of a coronary artery and a blood flow volume of the myocardium. Here, as a method of evaluating the microcirculation resistance, a method of evaluating blood flow in a capillary of a finger by applying laser light to a tip of the finger or the like has been known.

BRIEF DESCRIPTION OF THE DRAWINGS

FIG. 17 is a diagram for explaining an example of determination criteria for determining a therapeutic strategy according to the first embodiment.

DETAILED DESCRIPTION

According to an embodiment, a medical information processing system includes processing circuitry. The processing circuitry is configured to acquire a blood-vessel blood flow index in a coronary artery and a myocardial blood flow index in a myocardial region to which the coronary artery supplies blood. The processing circuitry is configured to calculate an index indicating a capability to supply the blood to the myocardial region by combining the blood-vessel blood flow index and the myocardial blood flow index.

Embodiments of a medical information processing system and a medical information processing method according to the present application will be described in detail below with reference to the accompanying drawings. The medical information processing system and the medical information processing method according to the present application are not limited by the embodiments described below. Further, in the following, a medical information processing apparatus will be described as an example of the medical information processing system.

First Embodiment

Figure 1:
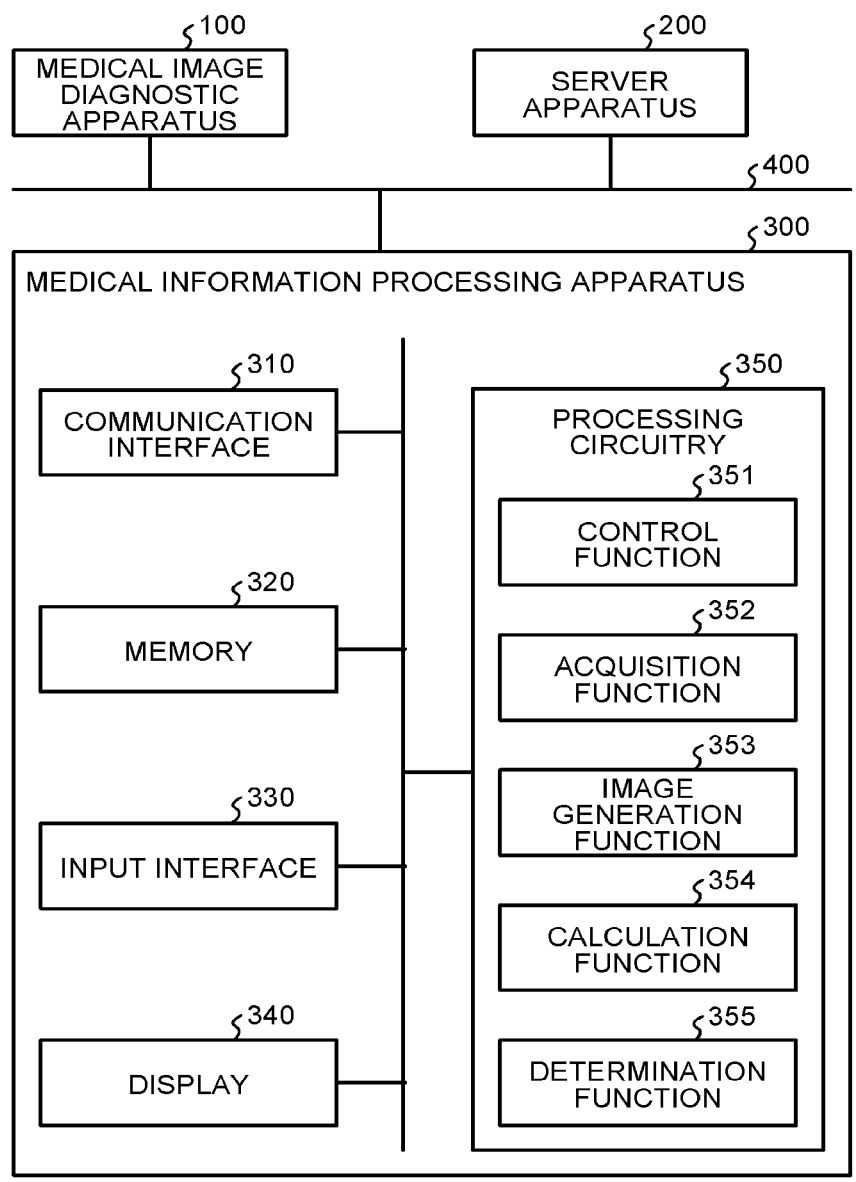
FIG. 1 is a diagram illustrating an example of a configuration of a medical information processing apparatus according to a first embodiment.

FIG. 1 is a diagram illustrating an example of a configuration of a medical information processing apparatus 300 according to a first embodiment. As illustrated in FIG. 1, the medical information processing apparatus 300 according to the first embodiment is connected to a medical image diagnostic apparatus 100 and a server apparatus 200 via a network 400. The example illustrated in FIG. 1 is one example, and various other devices, (for example, a terminal device and the like) may be connected to the network 400.

The medical image diagnostic apparatus 100 is an X-ray diagnostic apparatus, an X-ray computed tomography (CT) apparatus, a magnetic resonance imaging (MRI) apparatus, an ultrasonic diagnostic apparatus, a single photon emission computed tomography (SPECT) apparatus, a positron emission computed tomography (PET) apparatus, a SPECT-CT apparatus in which an SPECT apparatus and an X-ray CT apparatus are integrated, a PET-CT apparatus in which a PET apparatus and an X-ray CT apparatus are integrated, a group of the above-described apparatuses, or the like. Further, the medical image diagnostic apparatus 100 according to the first embodiment is able to generate three-dimensional medical image data (volume data).

Here, the medical image diagnostic apparatus 100 collects medical image data by which quantity of a blood flow index (for example, a blood flow volume) of a coronary artery or a blood flow index (for example, a blood flow volume) of a myocardium can be determined. For example, an X-ray CT apparatus as the medical image diagnostic apparatus 100 rotates and moves an X-ray tube and the X-ray detector approximately about the heart of a subject to which a contrast agent is administered, detects X-rays that have transmitted through the subject, and collects projection data. Then, the X-ray CT apparatus generates time-series three-dimensional CT image data (volume data) on the basis of the collected projection data. As one example, the X-ray CT apparatus collects coronary angiography CT image data for calculating the blood flow volume of the coronary artery through fluid analysis, or myocardial contrast-enhanced CT image data for calculating the blood flow volume of the myocardium through perfusion analysis.

Then, the medical image diagnostic apparatus 100 transmits the collected medical image data to the medical information processing apparatus 300 in response to a request from the medical information processing apparatus 300. Further, the medical image diagnostic apparatus 100 is able to transmit results of various kinds of analysis performed on the collected medical image data to the medical information processing apparatus 300.

The server apparatus 200 is an apparatus that stores therein the medical image data collected by the medical image diagnostic apparatus (for example, CT image data, CT images, etc. collected by the X-ray CT apparatus), various kinds of examination information (for example, information on intravascular pressure measured by a pressure wire, etc.), and the like, and performs various kinds of image processing on the medical image data. Here, the server apparatus 200 stores the medical image data that is acquired from the medical image diagnostic apparatus 100 via the network 400, various kinds of examination information, and the like in a memory that is installed inside or outside of the apparatus. Further, the server apparatus 200 transmits the medical image data, various kinds of examination information, and the like stored in the memory to the medical information processing apparatus 300 in response to a request from the medical information processing apparatus 300.

The medical information processing apparatus 300 acquires the medical image data from the medical image diagnostic apparatus 100 or the server apparatus 200 via the network 400, and processes the acquired image data. Further, the medical information processing apparatus 300 acquires various kinds of examination information from the server apparatus 200 via the network 400, and performs various kinds of processing using the acquired examination information. For example, the medical information processing apparatus 300 is realized by a computer apparatus, such as a workstation.

For example, as illustrated in FIG. 1, the medical information processing apparatus 300 includes the communication interface 310, a memory 320, an input interface 330, a display 340, and processing circuitry 350.

The communication interface 310 is connected to the processing circuitry 350, and controls transmission of various kinds of data to and communication with the medical image diagnostic apparatus 100 or the server apparatus 200 via the network 400. For example, the communication interface 310 is realized by a network card, a network adapter, a network interface controller (NIC), or the like. As one example, the communication interface 310 receives the medical image data or the examination information from the medical image diagnostic apparatus 100 or the server apparatus 200, and outputs the received medical image data or the received examination information to the processing circuitry 350.

The memory 320 is connected to the processing circuitry 350 and stores therein various kinds of data. Further, the memory 320 stores therein various kinds of information used for processing performed by the processing circuitry 350, processing results obtained by the processing circuitry 350, various programs for implementing various functions by being read and executed by the processing circuitry 350, and the like. For example, the memory 320 is realized by a semiconductor memory device, such as a random access memory (RAM) or a flash memory, a hard disk, an optical disk, or the like. In the present embodiment, the memory 320 stores therein the medical image data, the examination information, and the like received from the medical image diagnostic apparatus 100 or the server apparatus 200.

The input interface 330 is connected to the processing circuitry 350, converts input operation received from an operator into an electrical signal, and outputs the electrical signal to the processing circuitry 350. In the present application, the input interface 330 is not limited to a device that includes a physical operation component, such as a mouse or a keyboard. For example, examples of the input interface include an electrical signal processing circuitry that receives an electrical signal corresponding to input operation from an external input device separated from the apparatus, and that outputs the electrical signal to a control circuitry.

The display 340 is connected to the processing circuitry 350 and displays various kinds of information and various images that are output from the processing circuitry 350. For example, the display 340 is realized by a liquid crystal monitor, a cathode ray tube (CRT) monitor, a touch panel, or the like. For example, the display 340 displays a graphical user interface (GUI) for receiving an instruction from the operator, various display images, and various processing results obtained by the processing circuitry 350.

The processing circuitry 350 controls each of the components included in the medical information processing apparatus 300, in accordance with the input operation that is received from the operator via the input interface 330. For example, the processing circuitry 350 is realized by a processor. In the present embodiment, the processing circuitry 350 stores, in the memory 320, the medical image data, the examination information, and the like that are output from the communication interface 310. Further, the processing circuitry 350 reads, from the memory 320, the medical image data or the examination information, performs various kinds of processing, and displays a processing result on the display 340.

With this configuration, the medical information processing apparatus 300 according to the present embodiment is able to provide an index by which a capability of blood supply to the myocardium can be evaluated. Specifically, the medical information processing apparatus 300 provides an index by which a capability including a force of a blood vessel to send blood to the myocardium and diffusion of the blood in the myocardium can be evaluated. In other words, the medical information processing apparatus 300 provides an index by which resistance in the capillary can be evaluated. For example, the medical information processing apparatus 300 calculates an index (hereinafter, referred to as a capillary resistance index) for evaluating resistance (microcirculation resistance) in a capillary that supplies blood flown from a coronary artery to the myocardium, by using a blood-vessel blood flow index (for example, a blood flow volume) in the coronary artery and a myocardial blood flow index (for example, a blood flow volume) in the myocardium.

As illustrated in FIG. 1, the processing circuitry 350 according to the present embodiment executes a control function 351, an acquisition function 352, an image generation function 353, a calculation function 354, and a determination function 355. Here, the processing circuitry 350 is one example of processing circuitry.

The control function 351 controls the entire medical information processing apparatus 300. Specifically, the control function 351 performs control of executing processes corresponding to various requests that are input via the input interface 330. For example, the control function 351 controls transmission and reception of medical image data or the like via the communication interface 310, storage of information in the memory 320, display of information (for example, a display image or an analysis result) on the display 340, and the like.

The acquisition function 352 acquires the blood-vessel blood flow index in the coronary artery and the myocardial blood flow index in a myocardial region to which the coronary artery supplies blood. For example, the acquisition function 352 acquires a blood-vessel blood flow volume in the coronary artery and a myocardial blood flow volume in the myocardial region to which the coronary artery supplies blood. In this case, for example, the acquisition function 352 acquires the blood-vessel blood flow volume in the coronary artery and the myocardial blood flow volume in the myocardial region, on the basis of the medical image data or the examination information acquired from the medical image diagnostic apparatus 100 or the server apparatus 200.

For example, the acquisition function 352 acquires the blood-vessel blood flow volume in the coronary artery by performing fluid analysis on coronary angiography CT image data that is acquired from the X-ray CT apparatus as the medical image diagnostic apparatus 100 or from the server apparatus 200. Further, the acquisition function 352 is also able to acquire the blood-vessel blood flow volume in the coronary artery by using fractional flow reserve (FFR) measured by a pressure wire, instantaneous FFR, or fluid analysis etc. on coronary angiography MR image data, instead of acquiring the blood-vessel blood flow volume through the fluid analysis. In the following, an example will be described in which the blood-vessel blood flow volume in the coronary artery is obtained by performing fluid analysis on the coronary angiography CT image data.

Meanwhile, FFR and instantaneous FFR are indices for estimating the degree of blood flow inhibition, and are defined by a ratio of a blood flow volume on a branched side and a blood flow volume on a peripheral side in a blood vessel. In actual measurement of FFR, a relationship between a blood flow volume and pressure in the blood vessel is handled so as to become a proportional relationship, and the measurement is performed by replacing the blood flow volume with the pressure. For example, in measurement of FFR, adenosine is administered to obtain a maximum hyperemia state (stressed state) such that the relationship between the blood flow volume and the pressure in the blood vessel becomes a proportional relationship, and the blood flow volume that defines FFR is replaced with the pressure. Furthermore, for example, in measurement of instantaneous FFR, adenosine is not administered and a time phase in which the relationship between the blood flow volume and the pressure in the blood vessel in a resting state becomes a proportional relationship is used, and the blood flow volume that defines instantaneous FFR is replaced with the pressure. Therefore, the acquisition function 352 acquires the blood-vessel blood flow volume in the coronary artery by converting a value of the pressure measured by a pressure wire into a value of the blood flow volume.

In a case where the blood-vessel blood flow volume is to be acquired by performing fluid analysis based on the coronary angiography CT image data, the acquisition function 352 reads, from the memory 320, the coronary angiography CT image data in a plurality of time phases collected over time, and performs image processing on the read coronary angiography CT image data in the plurality of time phases, to thereby extract time-series blood vessel shape data.

Here, the acquisition function 352 sets a target region for which an index value is to be calculated in a blood vessel region that is included in the coronary angiography CT image data. Specifically, the acquisition function 352 sets the target region in the blood vessel region in accordance with an instruction or image processing performed by an operator via the input interface 330. Details of setting of the target region will be described later. Then, the acquisition function 352 extracts, as blood vessel shape data of the set target region, a centerline of the blood vessel (coordinate information on the centerline), a cross-sectional area of the blood vessel and a lumen in a cross section perpendicular to the centerline, a distance from the centerline to an inner wall and a distance from the centerline to an outer wall in a cylinder direction in the cross section perpendicular to the centerline, or the like from the coronary angiography CT image data.

Further, the acquisition function 352 sets an analysis condition for the fluid analysis. Specifically, the acquisition function 352 sets, as the analysis condition, a physical property value of blood, a condition for iterative calculation, a default value of analysis, or the like. For example, the acquisition function 352 sets, as the physical property value of blood, a viscosity of blood, a density of blood, or the like. Furthermore, the acquisition function 352 sets, as the condition for iterative calculation, the maximum number of times of iteration in the iterative calculation, a relaxation coefficient, an allowable value of a residual error, or the like. Moreover, the acquisition function 352 sets, as the default value of analysis, a default value of the blood flow volume, pressure, fluid resistance, a pressure boundary, or the like. Various values used by the acquisition function 352 may be incorporated in the system in advance, or may be defined interactively by an operator.

Then, the acquisition function 352 calculates an index value related to blood flow of the blood vessel through fluid analysis using the coronary angiography CT image data. Specifically, the acquisition function 352 performs fluid analysis using the blood vessel shape data and the analysis condition, and calculates the index value related to the blood flow in the target region of the blood vessel. For example, the acquisition function 352 calculates the index value, such as pressure, a blood flow volume, a blood flow velocity, a vector, or a shear stress, for each of predetermined positions in the blood vessel, on the basis of the blood vessel shape data, such as contours of the lumen and an outer wall of the blood vessel, the cross-sectional area of the blood vessel, or the centerline of the blood vessel, and on the basis of the set condition, such as the physical property value of blood, the condition for iterative calculation, or the default value of analysis.

Further, for example, the acquisition function 352 acquires the myocardial blood flow volume in the myocardium by performing perfusion analysis on the myocardial contrast-enhanced CT image data that is acquired from the X-ray CT apparatus as the medical image diagnostic apparatus 100 or from the server apparatus 200. Meanwhile, the acquisition function 352 is able to acquire the myocardial blood flow volume in the myocardium by using myocardial scintigraphy using a SPECT apparatus, determination of quantity of the myocardial blood flow volume using a PET apparatus, perfusion analysis on the myocardial contrast-enhanced MR image data, or the like, instead of acquiring the myocardial blood flow volume through perfusion analysis based on the myocardial contrast-enhanced CT image data. In the following, an example will be described in which the myocardial blood flow volume in the myocardium is acquired by performing perfusion analysis on the myocardial contrast-enhanced CT image data.

In a case where the myocardial blood flow volume is to be acquired by performing perfusion analysis based on the myocardial contrast-enhanced CT image data, the acquisition function 352 reads, from the memory 320, the myocardial contrast-enhanced CT image data in a plurality of time phases collected over time during a period corresponding to a plurality of heart beats, and performs image processing on the read myocardial contrast-enhanced CT image data in the plurality of time phases, to thereby calculate the myocardial blood flow volume. For example, the acquisition function 352 calculates a time density curve (TDC) for each of pixels included in a left ventricular cavity (or an aorta) and the myocardium, on the basis of the myocardial contrast-enhanced CT image data in the plurality of time phases collected over time during a period corresponding to a plurality of heart beats. Then, the acquisition function 352 calculates the myocardial blood flow volume for each of the pixels of the myocardium on the basis of correspondence between the calculated TDC for each of the pixels of the myocardium with respect to the calculated TDC for each of the pixels of the left ventricular cavity (or the aorta). Accordingly, the acquisition function 352 is able to acquire the blood flow volume for each of positions in the myocardium. Meanwhile, the acquisition function 352 is also able to calculate, as the myocardial blood flow volume in a predetermined region, an average of myocardial blood flow volumes of a pixel group included in the predetermined region in the myocardium.

As described above, the acquisition function 352 is able to acquire the blood-vessel blood flow volume for each of positions of coronary arteries and the myocardial blood flow volume for each of positions in the myocardium by calculating the blood flow volume and the myocardial blood flow volume by using the CT image data. Here, the acquisition function 352 acquires the blood-vessel blood flow volume and the myocardial blood flow volume at a position designated by the operator. Specifically, the acquisition function 352 acquires the blood-vessel blood flow volume at a position of a coronary artery and the myocardial blood flow volume in a myocardial region, where the position and the region correspond to the target region for which the capillary resistance index is to be calculated. For example, the acquisition function 352 determines, as the target region for which the capillary resistance index is to be calculated, a distal end region of a coronary artery where stenosis is observed, a myocardial region where ischemia is observed, or a myocardial region to be subjected to medical examination, and acquires the blood flow volume and the myocardial blood flow volume at a corresponding position.

As one example, the acquisition function 352 acquires the blood-vessel blood flow volume in a coronary artery that is selected by the operator from among coronary arteries included in a display image generated by the image generation function 353. Then, the acquisition function 352 identifies a myocardial region to which the selected coronary artery supplies blood, and acquires the myocardial blood flow volume of the identified myocardial region. Here, the operator is able to designate a position at which the blood flow volume is to be acquired in the coronary artery. In other words, the operator is able to select the coronary artery for which the blood-vessel blood flow volume is to be acquired, and further select a position at which the blood-vessel blood flow volume is to be calculated in the selected blood vessel.

Meanwhile, if the position at which the blood-vessel blood flow volume is to be acquired is not designated (if only the coronary artery is selected), the acquisition function 352 may calculate the blood flow volume of a branched portion of the selected coronary artery. Further, a control region of the selected coronary artery is identified by, for example, the Voronoi method. In other words, the acquisition function 352 identifies the control region of the selected coronary artery by performing region expansion based on the shape of the selected coronary artery.

Further, for example, when the myocardial region is to be designated by the operator, the acquisition function 352 first identifies a coronary artery that supplies blood to the myocardial region designated by the operator. As one example, the acquisition function 352 identifies the coronary artery that supplies blood to the designated myocardial region on the basis of a morphological positional relationship between the coronary artery and the myocardium. Here, the acquisition function 352 is able to further identify a range of the coronary artery that supplies blood to the designated myocardial region. Then, the acquisition function 352 further identifies a control region of the selected coronary artery by performing region expansion based on the shape of the identified coronary artery, and acquires the myocardial blood flow volume in the identified control region.

Meanwhile, when the coronary artery that supplies blood to the designated myocardial region is identified, the acquisition function 352 calculates the blood-vessel blood flow volume of, for example, a branched portion of the identified coronary artery. Further, when the range of the coronary artery that supplies blood to the designated myocardial region is further identified, the acquisition function 352 calculates the blood-vessel blood flow volume of, for example, an end portion on the branched side in the range of the identified coronary artery.

The image generation function 353 reads the medical image data stored in the memory 320, and generates a display image from the read medical image data. For example, the image generation function 353 reads CT image data, performs various kinds of image processing on the read CT image data, and generates a display image of the entire heart, a coronary artery, and a partial myocardial region. As one example, the image generation function 353 performs image processing on the CT image data, and generates a volume-rendered image, a curved multi planer reconstruction (CPR) image, a multi planer reconstruction (MPR) image, a stretched multi planer reconstruction (SPR) image, a polar map, or the like.

Further, the image generation function 353 generates display information using the blood-vessel blood flow volume, the myocardial blood flow volume, or the examination result, such as FFR, that is acquired by the acquisition function 352, the capillary resistance index that is calculated by the calculation function 354, or the like. For example, the image generation function 353 generates a perfusion image representing the myocardial blood flow volume, a graph representing the capillary resistance index, or the like.

Figure 2:
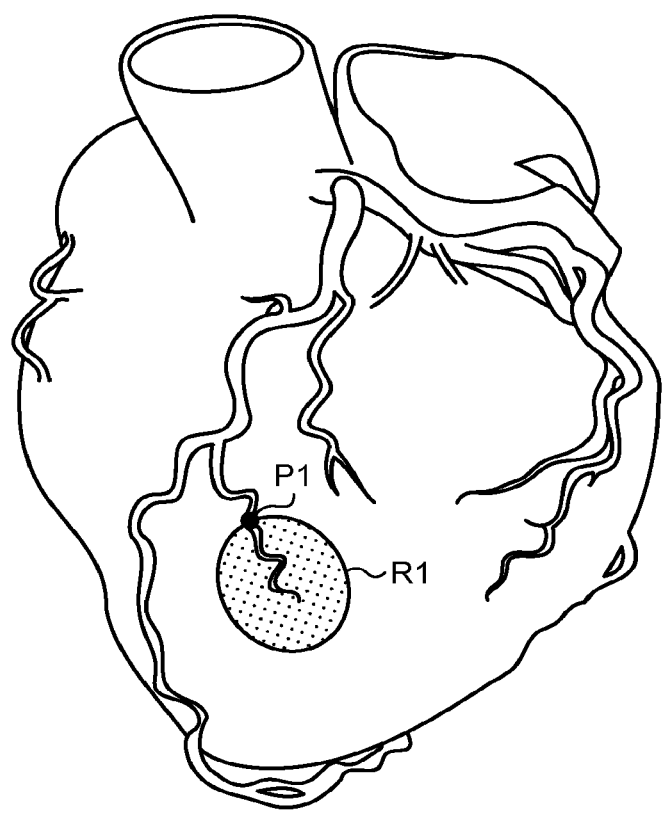
FIG. 2 is a diagram for explaining an example of calculation of a capillary resistance index by the medical information processing apparatus according to the first embodiment.

The calculation function 354 calculates an index indicating a capability of blood supply to the myocardial region by combining the blood-vessel blood flow index and the myocardial blood flow index. Specifically, the calculation function 354 calculates an index indicating a capability including a force of a blood vessel to send blood to the myocardial region and diffusion of the blood in the myocardial region. For example, the calculation function 354 calculates the capillary resistance index indicating an amount of capillary resistance in a capillary that supplies blood to the myocardial region, by combining the blood-vessel blood flow volume and the myocardial blood flow volume. As one example, the calculation function 354 calculates the capillary resistance index based on a ratio of the blood-vessel blood flow volume and the myocardial blood flow volume. FIG. 2 is a diagram for explaining calculation of the capillary resistance index by the medical information processing apparatus 300 according to the first embodiment.

Here, in FIG. 2, a case is illustrated in which a blood-vessel blood flow volume at a position P1 in a coronary artery and a myocardial blood flow volume in a myocardial region R1 are acquired. As described above, the position P1 and the region R1 may be determined by the operator by designating the coronary artery, or may be determined by the operator by designating the myocardial region.

The calculation function 354 calculates a capillary resistance index corresponding to the position P1 in the coronary artery and the myocardial region R1, by using the blood-vessel blood flow volume at the position P1 in the coronary artery and the myocardial blood flow volume in the myocardial region R1. For example, the calculation function 354 calculates the capillary resistance index using Equation below.

Capillary Resistance Index=Myocardial Blood Flow Volume ($Q_{myo}$)/Blood-vessel Blood Flow Volume ($Q_{vessel}$)

That is, the calculation function 354 is able to calculate a capability to supply blood from the coronary artery to the myocardial region (a degree of blood flow inhibition in a capillary between the coronary artery and the myocardium) by calculating a ratio of the blood-vessel blood flow volume in the coronary artery and the myocardial blood flow volume in the myocardial region controlled by the coronary artery. Here, for example, if the capillary resistance is increased, blood supply from the coronary artery to the myocardial region is reduced, so that the capillary resistance index becomes smaller than "1". In contrast, if the capillary resistance is reduced, blood supply from the coronary artery to the myocardial region is not reduced, so that the capillary resistance index approaches "1".

For example, the calculation function 354 calculates the capillary resistance index corresponding to the position P1 and the myocardial region R1, on the basis of Equation as described above by using the "blood-vessel blood flow volume ($Q_{vessel}$)" at the position P1 and the "myocardial blood flow volume ($Q_{myo}$)" in the myocardial region R1 that are acquired by the acquisition function 352.

In the above-described embodiment, the case has been described in which the capillary resistance index is calculated for a single coronary artery and a corresponding region. However, embodiments are not limited to this example, and the medical information processing apparatus 300 is able to calculate a capillary resistance index for a myocardial region that is controlled by a plurality of coronary arteries. In this case, for example, the acquisition function 352 acquires a plurality of blood-vessel blood flow volumes in a plurality of coronary arteries and a single myocardial blood flow volume in which a plurality of myocardial blood flow volumes in a plurality of myocardial regions to which the respective coronary arteries supply blood are combined. Then, the calculation function 354 calculates the capillary resistance index by combining the plurality of blood-vessel blood flow volumes and the single myocardial blood flow volume.

Figure 3:
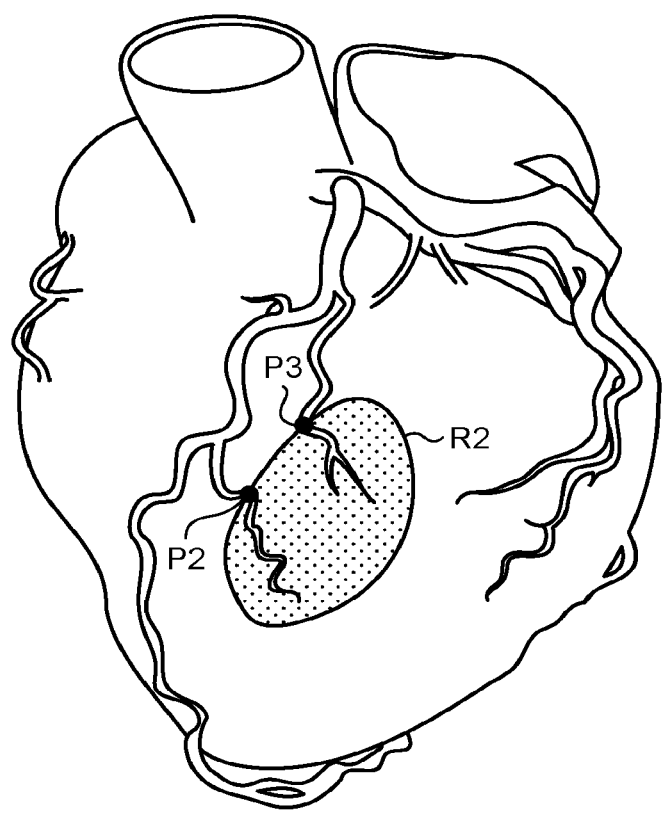
FIG. 3 is a diagram for explaining an example of calculation of the capillary resistance index by the medical information processing apparatus according to the first embodiment.

FIG. 3 is a diagram for explaining an example of calculation of the capillary resistance index by the medical information processing apparatus 300 according to the first embodiment. Here, in FIG. 3, a case is illustrated in which a capillary resistance index of a myocardial region controlled by two coronary arteries is calculated. For example, in the example as illustrated in FIG. 3, if a target region for calculating the capillary resistance index is designated, the acquisition function 352 identifies ranges of the two coronary arteries that supply blood to the designated target region. Then, the acquisition function 352 acquires a blood-vessel blood flow volume "$Q_{vessel1}$" at a position P2 and a blood-vessel blood flow volume "$Q_{vessel2}$" at a position P3 in end portions on the branched side in the identified ranges of the two respective coronary arteries.

Furthermore, the acquisition function 352 identifies, by the Voronoi method, a control region corresponding to the identified range of each of the two coronary arteries, and extracts a single region R2 in which the identified control regions are integrated. Then, the acquisition function 352 acquired the myocardial blood flow volume "$Q_{myo}$" in the extracted region R2. Meanwhile, determination of the position P2, the position P3, and the region R2 are described by way of example only, and, for example, the operator may designate the position P2 and the position P3 and the acquisition function 352 may identify the region R2 on the basis of the designated positions P2 and P3.

As described above, if the acquisition function 352 acquires the blood-vessel blood flow volume "$Q_{vessel1}$" at the position P2, the blood-vessel blood flow volume "$Q_{vessel2}$" at the position P3, and the myocardial blood flow volume "$Q_{myo}$" in the region R2, the calculation function 354 calculates a capillary resistance index in the region R2 such that, for example, "the myocardial blood flow volume ($Q_{myo}$)/(the blood flow volume ($Q_{vessel1}$)+the blood flow volume ($Q_{vessel2}$))".

In the above-described example, the case has been described in which when a range for supplying blood to the myocardial region is to be identified, only an end portion on the branched side is identified. However, embodiments are not limited to this example, and, for example, it may be possible to identify an end portion on the branched side and an end portion on the peripheral side. In this case, the acquisition function 352 acquires a blood-vessel blood flow volume in an end portion on an upstream side and a blood-vessel blood flow volume in an end portion on a downstream side of a certain range of the coronary artery that supplies blood to the myocardial region, and acquires a myocardial blood flow volume in the designated myocardial region. Then, the calculation function 354 calculates an index by combining a difference between the blood-vessel blood flow volume in the end portion on the upstream side and the blood-vessel blood flow volume in the end portion on the downstream side and the myocardial blood flow volume in the designated myocardial region.

Figure 4:
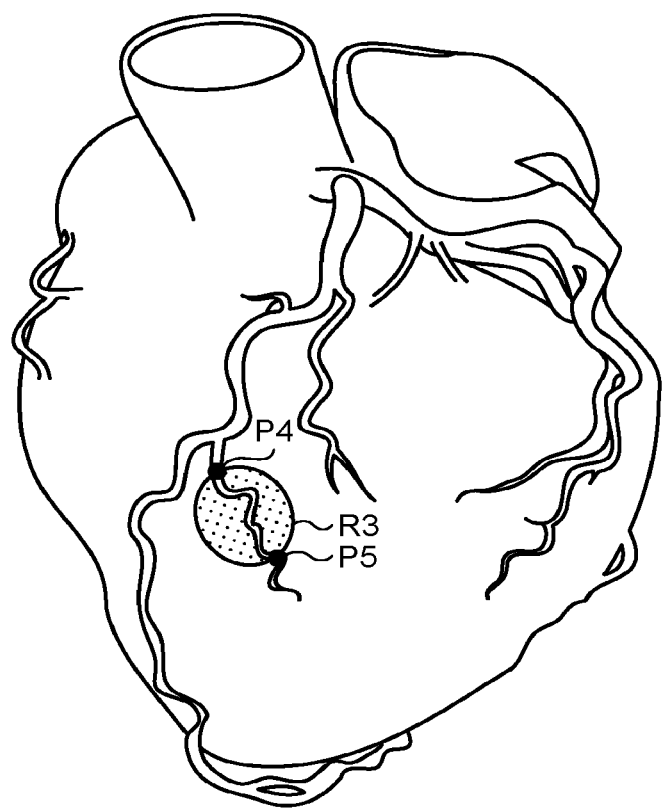
FIG. 4 is a diagram for explaining an example of calculation of the capillary resistance index by the medical information processing apparatus according to the first embodiment.

FIG. 4 is a diagram for explaining an example of calculation of the capillary resistance index by the medical information processing apparatus 300 according to the first embodiment. In FIG. 4, a case is illustrated in which a capillary resistance index in a myocardial region that is controlled by a predetermined range of a single coronary artery is calculated. For example, in the example illustrated in FIG. 4, if a target region for calculating the capillary resistance index is designated in a predetermined range of a single coronary artery, the acquisition function 352 identifies a range of the coronary artery (the end portion on the branched side and the end portion on the peripheral side of the coronary artery) that supplies blood to the designated target region. Then, the acquisition function 352 acquires a blood-vessel blood flow volume "$Q_{vessel3}$" at a position P4 in the end portion on the branched side and a blood-vessel blood flow volume "$Q_{vessel4}$" at a position P5 in the identified range of the coronary artery. Further, the acquisition function 352 calculates "$Q_{vessel3}-Q_{vessel4}$" as the blood-vessel blood flow volume in the range from the position P4 to the position P5 in the coronary artery.

Subsequently, the acquisition function 352 identifies, by the Voronoi method, a myocardial region R3 that is controlled by the identified range of the coronary artery. Then, the acquisition function 352 acquires the myocardial blood flow volume "$Q_{myo}$" in the identified region R3. Meanwhile, determination of the position P4, the position P5, and the region R3 are described by way of example only, and, for example, the operator may designate the position P4 and the position P5 and the acquisition function 352 may identify the region R3 on the basis of the designated positions P4 and P5.

As described above, if the acquisition function 352 acquires the blood-vessel blood flow volume "$Q_{vessel3}-Q_{vessel4}$" in the range from the position P4 to the position P5 in the coronary artery and the myocardial blood flow volume "$Q_{myo}$" in the region R3, the calculation function 354 calculates a capillary resistance index corresponding to the range from the position P4 to the position P5 in the coronary artery and the region R3 such that, for example, "the myocardial blood flow volume ($Q_{myo}$) in the region R3/(the blood flow volume ($Q_{vessel3}$)-the blood flow volume ($Q_{vessel4}$))".

In the above-described example, the case has been described in which the capillary resistance index is calculated for a single myocardial region. However, embodiments are not limited to this example, and, for example, it may be possible to divide the myocardial region into partial regions, and calculate a capillary resistance index in each of the divided partial regions. In this case, the acquisition function 352 divides a coronary artery and a myocardial region to which the coronary artery supplies blood into a plurality of ranges, and acquires, for each of the divided ranges, and acquires, for each of the divided ranges, a blood-vessel blood flow volume in an end portion on the upstream side and a blood-vessel blood flow volume in an end portion on the downstream side of each of the ranges and a myocardial blood flow volume in a myocardial region corresponding to each of the ranges. Then, the calculation function 354 calculates a capillary resistance index for each of the divided ranges by combining a difference between the blood-vessel blood flow volume in the end portion on the upstream side and the blood-vessel blood flow volume in the end portion on the downstream side and the myocardial blood flow volume in the myocardial region corresponding to each of the ranges.

Figure 5A:
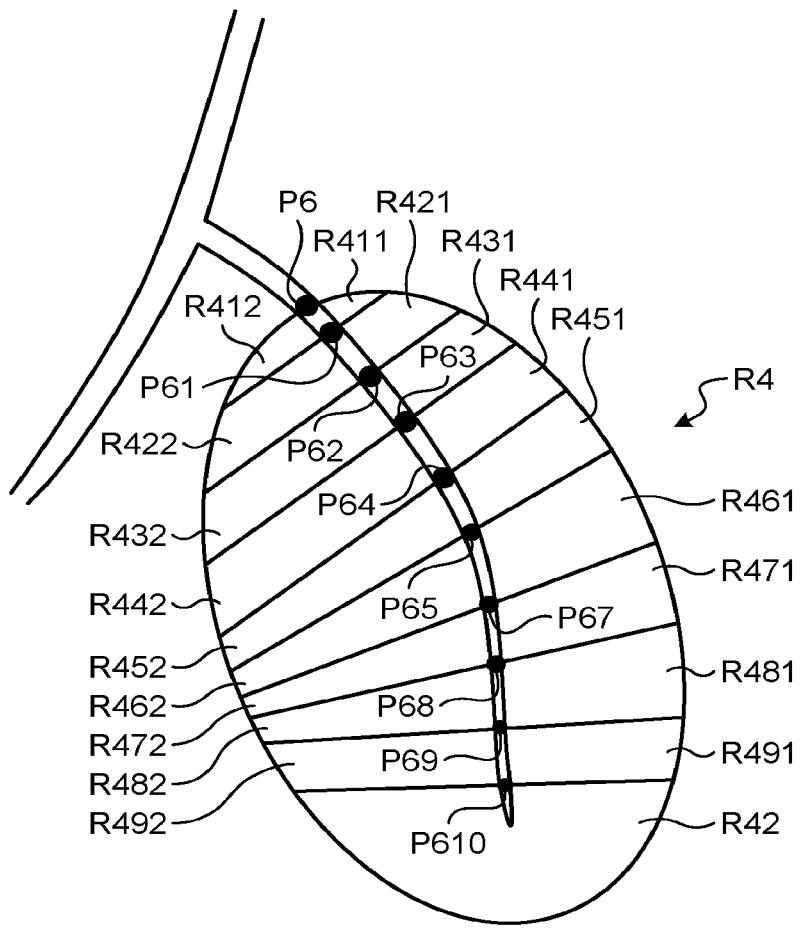
FIG. 5A is a diagram for explaining an example of calculation of the capillary resistance index by the medical information processing apparatus according to the first embodiment.

FIG. 5A is a diagram for explaining an example of calculation of the capillary resistance index by the medical information processing apparatus 300 according to the first embodiment. In FIG. 5A, a case is illustrated in which a myocardial region controlled by a coronary artery is divided into a plurality of partial regions and a capillary resistance index is calculated for each of the partial regions. For example, in the example illustrated in FIG. 5A, if a target region for calculating the capillary resistance index is designated, the acquisition function 352 identifies a range of the coronary artery (a position P6 in an end portion on the branched side of the coronary artery) that supplies blood to the designated target region. Then, the acquisition function 352 identifies, by the Voronoi method, a myocardial region R4 that is controlled by the identified range of the coronary artery.

Thereafter, the acquisition function 352 acquires the centerline of the identified range of the coronary artery, and divides the coronary artery and the myocardial region R4 into a plurality of ranges in a direction perpendicular to the centerline. As one example, the acquisition function 352 divides a partial region R411 and a partial region R412 from the region R4 by a line segment that is perpendicular to the centerline of the coronary artery and that passes through a position P61. In other words, the acquisition function 352 divides, by the line segment that passes through the position P61, a range including a region from the position P6 to the position P61 in the coronary artery and including the partial region R411 and the partial region R412, from the coronary artery and the region R4.

Further, the acquisition function 352 divides a partial region R421 and a partial region R422 from the region R4 and divides a region from the position P61 to the position P62 from the coronary artery, by a line segment that is perpendicular to the centerline of the coronary artery and that passes through a position P62. Similarly, the acquisition function 352 divides partial regions R431 to R492 and a partial region R42 by line segments that pass through positions P63 to P610, respectively.

Then, the acquisition function 352 acquires a blood-vessel blood flow volume and a myocardial blood flow volume for each of the divided ranges. As one example, the acquisition function 352 acquires the blood-vessel blood flow volume and the myocardial blood flow volume for a range including the region from the position P6 to the position P61 in the coronary artery and including the partial region R411 and the partial region R412. For example, the acquisition function 352 acquires a blood-vessel blood flow volume "$Q_{vessel6}$" at the position P6 and a blood-vessel blood flow volume "$Q_{vessel61}$" at the position P61. Furthermore, the acquisition function 352 calculates "$Q_{vessel6}-Q_{vessel61}$" as the blood-vessel blood flow volume in the region from the position P6 to the position P61 in the coronary artery. Moreover, the acquisition function 352 acquires a myocardial blood flow volume "$Q_{myo411}$" in the partial region R411 and a myocardial blood flow volume "$Q_{myo421}$" in the partial region R421.

Similarly, the acquisition function 352 acquires a blood-vessel blood flow volume and a myocardial blood flow volume for each of the ranges, i.e., from the range including the region from the position P61 to the position P62 in the coronary artery, the partial region R421, and the partial region R422 to the range including the region from the position P610 to a distal end of the coronary artery in the coronary artery and the partial region R42.

The calculation function 354 calculates a capillary resistance index for each of the partial regions by using the blood-vessel blood flow volume for each of the ranges acquired by the acquisition function 352 and the myocardial blood flow volume in the partial region. For example, the calculation function 354 calculates "$Q_{myo411}/(Q_{vessel6}-Q_{vessel61})$" as a capillary resistance index in the partial region R411. Further, the calculation function 354 calculates "$Q_{myo421}/(Q_{vessel6}-Q_{vessel61})$" as a capillary resistance index in the partial region R421. Meanwhile, the calculation function 354 may calculate, as the capillary resistance index corresponding to the region from the position P6 to the position P61 in the coronary artery, an average of the capillary resistance index in the partial region R411 and the capillary resistance index in the partial region R421, for example.

Similarly, the calculation function 354 calculates a capillary resistance index for each of the partial regions for each of ranges, i.e., from the range including the region from the position P61 to the position P62 in the coronary artery, the partial region R421, and the partial region R422 to the range including the region from the position P610 to the distal end of the coronary artery in the coronary artery and the partial region R42. Meanwhile, as for the range including the region from the position P610 to the distal end of the coronary artery in the coronary artery and the partial region R42, a single capillary resistance index is calculated from a myocardial blood flow volume in the region from the position P610 to the distal end of the coronary artery in the coronary artery and a myocardial blood flow volume in the partial region R42.

The example of division illustrated in FIG. 5A is one example, and embodiments are not limited thereto. In other words, the number of partial regions to be divided from the region R4 is not limited to the number as illustrated in FIG. 5A, but it may be possible to divide the region into a larger number of partial regions than the number as illustrated in FIG. 5A or into a smaller number of partial regions than the number as illustrated in FIG. 5A, for example.

Figure 5B:
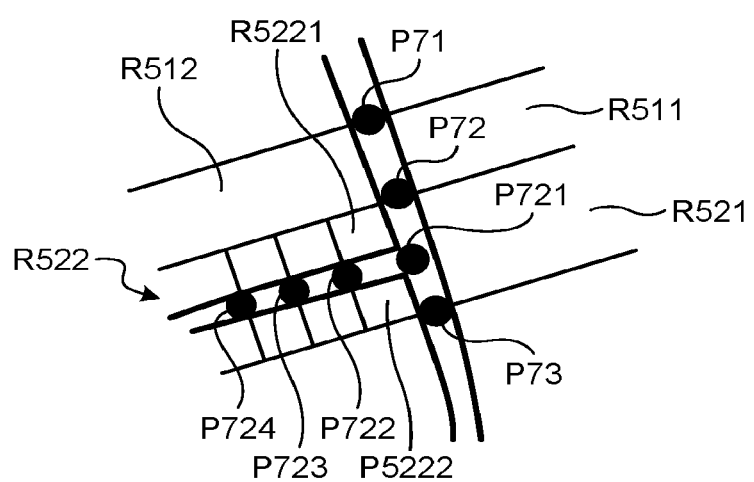
FIG. 5B is a diagram for explaining an example of calculation of the capillary resistance index by the medical information processing apparatus according to the first embodiment.

In the above-described example, the case has been described in which a control region of a single coronary artery is divided. In the following, a case will be described in which a control region corresponding to a region in which a coronary artery is branched will be described. FIG. 5B is a diagram for explaining an example of calculation of the capillary resistance index by the medical information processing apparatus 300 according to the first embodiment. In FIG. 5B, an enlarged view of the region in which a coronary artery is branched is illustrated. In other words, even in the case as illustrated in FIG. 5B, in reality, a range of the coronary artery and a myocardial region controlled by the range of the coronary artery are identified in the same manner as illustrated in FIG. 5A.

For example, in the example illustrated in FIG. 5B, the acquisition function 352 first divides a range including a region from a position P71 to a position P72 in a coronary artery, a partial region R511, and a partial region R512, and divides a range including a region from the position P72 to a position P73 in the coronary artery, a partial region R521, and a partial region R522. Then, the acquisition function 352 further divides the partial region R522 including a branch into a plurality of ranges. For example, the acquisition function 352 divides, from the partial region R522, a range including a region from a position P721 to a position P722 in the coronary artery, a partial region R5221, and a partial region R5222. Similarly, the acquisition function 352 divides a plurality of ranges from the partial region R522 including the branch.

If division as described above is performed, the acquisition function 352 acquires a blood-vessel blood flow volume and a myocardial blood flow volume for each of the ranges. In other words, the acquisition function 352 acquires, for each of the divided ranges, the blood-vessel blood flow volume in the coronary artery and the myocardial blood flow volume in each of the partial regions. For example, as for the range including the region from the position P71 to the position P72 in the coronary artery, the partial region R511, and the partial region R512, the acquisition function 352 acquires a blood-vessel blood flow and a myocardial blood flow volume in the same manner as described above with reference to FIG. 5A.

Further, as for the range including the region from the position P72 to the position P73 in the coronary artery, the partial region R521, and the partial region R522 with the branch, the acquisition function 352 acquires a blood flow volume for each of the region as described below, for example. First, as a blood flow volume for calculating a capillary resistance index in the partial region R521 that does not include the branch, the acquisition function 352 acquires a blood-vessel blood flow volume"$Q_{vessel72}$" at the position P72 and a blood-vessel blood flow volume "$Q_{vessel73}$" at the position P73 in the same manner as described above with reference to FIG. 5A. Further, the acquisition function 352 calculates "$Q_{vessel72}-Q_{vessel73}$" as a blood-vessel blood flow volume in the region from the position P72 to the position P73 in the coronary artery. Furthermore, the acquisition function 352 acquires a myocardial blood flow volume "$Q_{myo521}$" in the partial region R521.

In contrast, as a blood flow volume for calculating a capillary resistance index in the partial region R522 that includes the branch, the acquisition function 352 acquires the blood-vessel blood flow volume "$Q_{vessel72}$" at the position P72, a blood-vessel blood flow volume "$Q_{vessel721}$" at a branch position P721, the blood-vessel blood flow volume "$Q_{vessel73}$" at the position P73, a blood-vessel blood flow volume "$Q_{vessel722}$" at the position P722, a blood-vessel blood flow volume"$Q_{vessel723}$" at a position P723, and a blood-vessel blood flow volume "$Q_{vessel724}$" at a position P724. Then, the acquisition function 352 calculates a blood-vessel blood flow volume "$Q_{vessel72}-Q_{vessel721}$" in the region from the position P72 to the position P721 in the coronary artery, a blood-vessel blood flow volume "$Q_{vessel721}-Q_{vessel73}$" in the region from the position P721 to the position P73 in the coronary artery, a blood-vessel blood flow volume "$Q_{vessel721}-Q_{vessel722}$" in the region from the position P721 to the position P722 in the coronary artery, a blood-vessel blood flow volume "$Q_{vessel722}-Q_{vessel723}$" in the region from the position P722 to the position P723 in the coronary artery, and the blood-vessel blood flow volume "$Q_{vessel723}-Q_{vessel724}$" in the region from the position P723 to the position P724 in the coronary artery.

Furthermore, the acquisition function 352 acquires myocardial blood flow volume in each of the partial regions that are divided from the partial region R522 that includes a myocardial blood flow volume "$Q_{myo5221}$" in the partial region R5221 and a myocardial blood flow volume "$Q_{myo5221}$" in the partial region R5221.

As described above, if the blood flow volume in each of the regions is acquired, the calculation function 354 calculates a capillary resistance index for each of the divided ranges by using each of the blood flow volumes. For example, as for the range including the region from the position P71 to the position P72 in the coronary artery, the partial region R511, and the partial region R512, the calculation function 354 calculates the capillary resistance index in the same manner as described above with reference to FIG. 5A.

In contrast, as for the range including the partial region R522 that includes the branch, the calculation function 354 calculates the capillary resistance index as described below, for example. First, as for the capillary resistance index in the partial region R521 that does not include the branch, the calculation function 354 calculates "$Q_{myo521}/(Q_{vessel72}-Q_{vessel73})$" in the same manner as described above with reference to FIG. 5A.

Then, as for the capillary resistance index in each of the partial regions included in the partial region R522 that includes the branch, the calculation function 354 calculates, for example, the capillary resistance index in the partial region R5221 such that "$Q_{myo5221}/((Q_{vessel72}-Q_{vessel721})+(Q_{vessel721}-Q_{vessel722}))$". In other words, the calculation function 354 calculates the capillary resistance index by taking into account blood supply from the region between the position P72 and the position P721 in the coronary artery and blood supply from the region between the position P721 to the position P722 in the coronary artery.

Similarly, the calculation function 354 calculates, as the capillary resistance index in the partial region R5222, a capillary resistance index such that "$Q_{myo5222}/(Q_{vessel721}-Q_{vessel73})+(Q_{vessel721}-Q_{vessel722}))$" by taking into account blood supply from the region between the position P721 and the position P73 in the coronary artery and blood supply from the region between the position P721 and the position P722 in the coronary artery, for example. The indices in the other ranges are calculated in the same manner as described above. In other words, for example, as for the range from the position P722 to the position P723, the calculation function 354 calculates the capillary resistance index for each of the partial regions on both sides by calculating a blood-vessel blood flow volume "$Q_{vessel722}-Q_{vessel723}$" in the region from the position P722 to the position P723 in the coronary artery with respect to a myocardial blood flow volume in each of the partial regions on both sides.

The example of division illustrated in FIG. 5B is one example, and embodiments are not limited thereto. In other words, the number of partial regions to be divided is not limited to the number as illustrated in FIG. 5B, but it may be possible to divide the region into a larger number of partial regions than the number as illustrated in FIG. 5B or into a smaller number of partial regions than the number as illustrated in FIG. 5B, for example.

As described above, the acquisition function 352 and the calculation function 354 according to the present embodiment calculate the capillary resistance index from the blood-vessel blood flow volume in the coronary artery and the myocardial blood flow volume in the myocardium. Here, the calculation of the capillary resistance index as described above may be applied to the entire heart. In other words, the acquisition function 352 and the calculation function 354 are able to calculate the capillary resistance index with respect to a myocardium of the entire heart, a right coronary artery (RCA), a left anterior descending coronary artery (LAD), and a left circumflex coronary artery (LCX) including all of branched blood vessels.

Meanwhile, the operator is able to arbitrarily perform settings of the target region for calculating the capillary resistance index, settings as to whether to divide the target region, settings of the number of parts to be divided, and the like. For example, the settings may be arbitrarily made for each of capillary resistance indices to be calculated. Further, it may be possible to set conditions in advance for each of target regions for calculating the capillary resistance indices. In this case, for example, if a myocardial region in a ventricular apex is set as a target region, it may be possible to set conditions in advance so as to calculate the capillary resistance index by using blood-vessel blood flow volumes in three blood vessels in the RCA, the LAD and the LCX.

Furthermore, the blood-vessel blood flow volume and the myocardial blood flow volume as described above may be acquired in any of a stressed state and a resting state. In other words, the acquisition function 352 and the calculation function 354 according to the present embodiment are able to calculate a capillary resistance index in the stressed state and a capillary resistance index in the resting state.

Referring back to FIG. 1, the determination function 355 determines a state of the target region on the basis of the capillary resistance index calculated by the calculation function 354. For example, the determination function 355 determines whether microcirculation is adequately maintained in blood supply to the myocardium by comparing the calculated capillary resistance index value and a threshold. As one example, if the capillary resistance index value is smaller than a predetermined threshold, the determination function 355 determines that blood supply in the capillary is inhibited.

Further, for example, the determination function 355 may be able to determine the state of the target region by comparing capillary resistance indices calculated in the stressed state and the resting state. As one example, if capillary resistance indices that are calculated in the stressed state and the resting state of a region in which ischemia occurs are compared and have no differences, the determination function 355 determines that a defect has occurred in the coronary artery.

Furthermore, for example, the determination function 355 may determine a therapeutic strategy by using the capillary resistance index and other kinds of examination information. Determination of the therapeutic strategy will be described in detail later.

As described above, the medical information processing apparatus 300 according to the present embodiment is able to calculate the capillary resistance index with respect to the entire heart. Further, the medical information processing apparatus 300 is able to display the calculated capillary resistance index in various modes. In other words, the control function 351 is able to display, on the display 340, information on the capillary resistance index calculated by the calculation function 354. In the following, examples of a display mode of the capillary resistance index according to the present embodiment will be described with reference to FIG. 6 to FIG. 16. FIG. 6 to FIG. 16 are diagrams illustrating examples of the display mode of the capillary resistance index according to the first embodiment.

Figure 6:
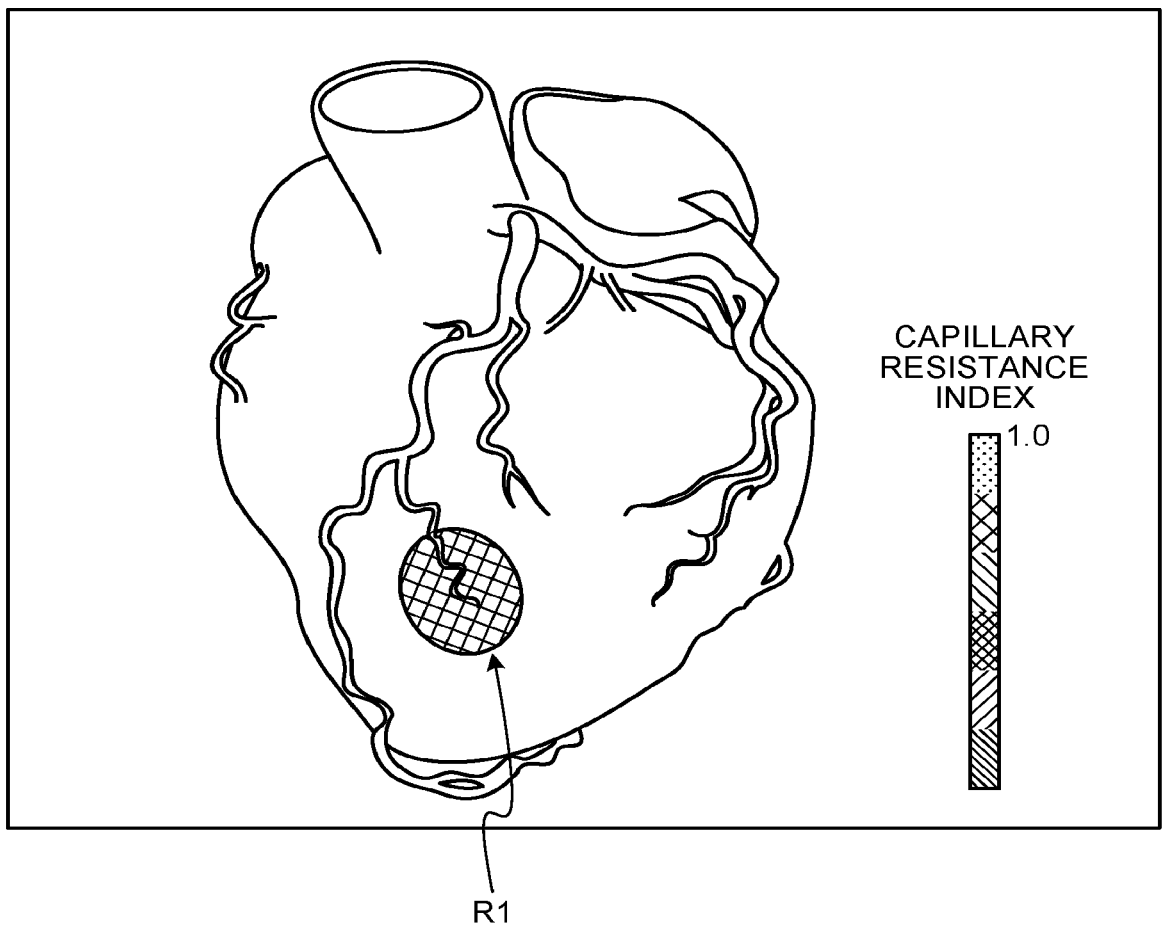
FIG. 6 is a diagram illustrating an example of a display mode of the capillary resistance index according to the first embodiment.

For example, the control function 351 performs control of displaying a display image indicating information on the capillary resistance index calculated by the calculation function 354, on a medical image that includes at least one of the myocardial region and the coronary artery. As one example, as illustrated in FIG. 6, the control function 351 displays a color image in which a region R1 on a volume-rendered image of the entire heart is represented in a certain color corresponding to a value of the calculated capillary resistance index.

In this case, the image generation function 353 generates the volume-rendered image of the entire heart from the acquired CT image data, for example. The control function 351 displays the color image in which the region R1 of the generated volume-rendered image is represented in a certain color corresponding to the value of the calculated capillary resistance index. Meanwhile, colors can be arbitrarily assigned to capillary resistance indices. The example illustrated in FIG. 6 is one example, and various other images may be used as the display image. For example, it may be possible to use a surface-rendered image.

Figure 7A:
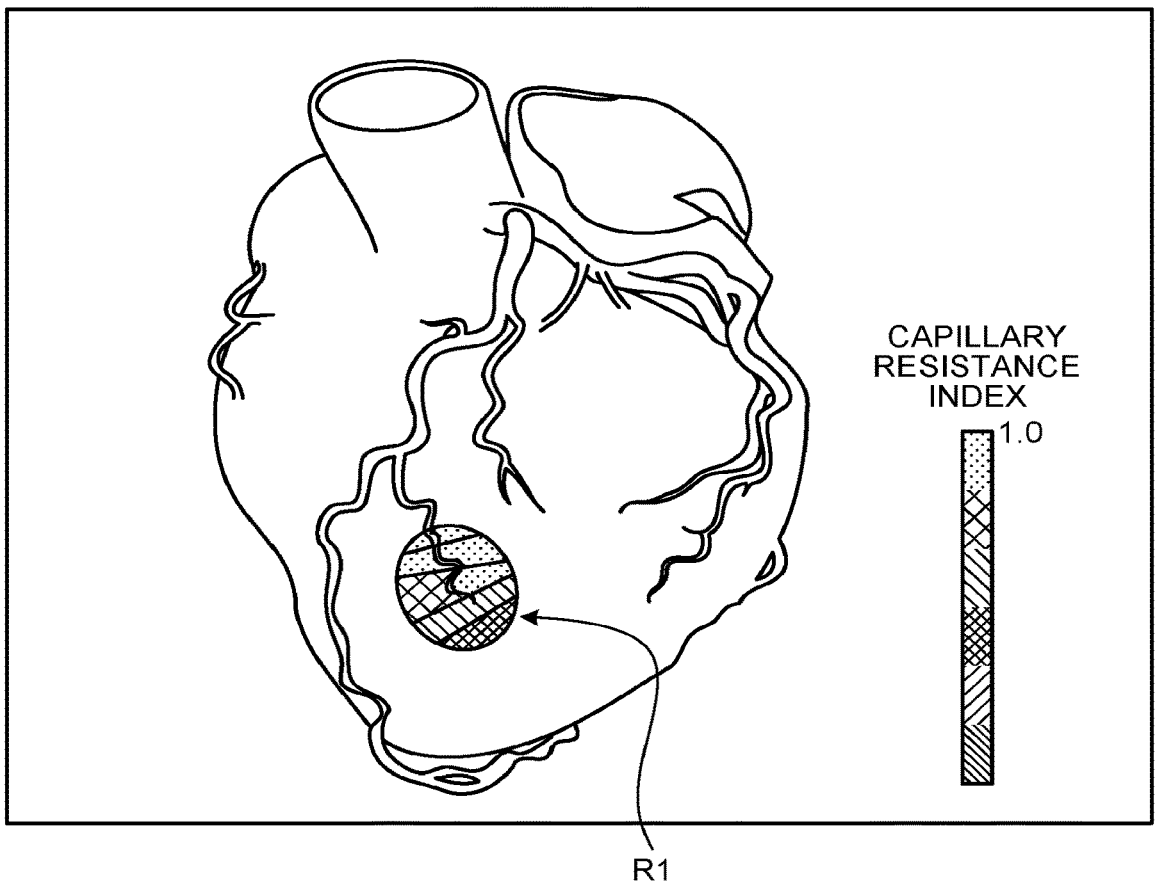
FIG. 7A is a diagram illustrating an example of a display mode of the capillary resistance index according to the first embodiment.

Furthermore, the control function 351 performs control of displaying a color image in which capillary resistance indices calculated for the respective divided ranges are represented in certain colors and allocated on a three-dimensional image of the myocardial region or the coronary artery. For example, if the target region is divided into partial regions and capillary resistance indices are calculated for the respective partial regions, the control function 351 displays, as illustrated in FIG. 7A, a color image in which the divided partial regions are represented in certain colors corresponding to values of the capillary resistance indices calculated for the respective partial regions in the region R1 on a volume-rendered image of the myocardium.

Figure 7B:
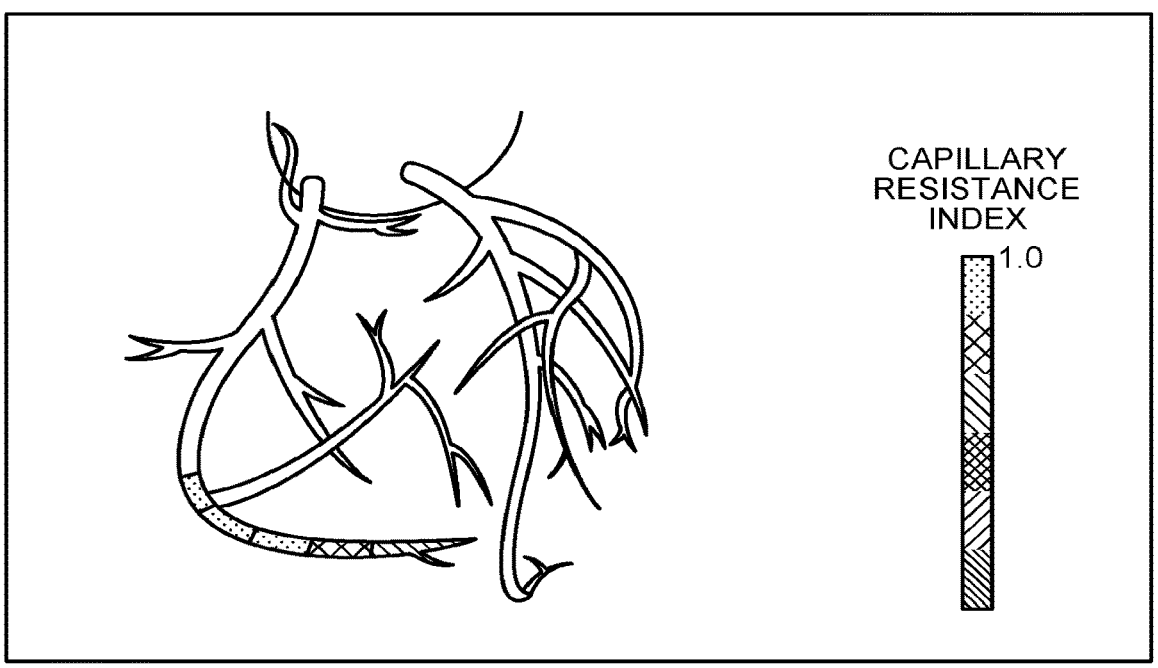
FIG. 7B is a diagram illustrating an example of a display mode of the capillary resistance index according to the first embodiment.

Moreover, for example, if the target region is divided into partial regions and capillary resistance indices are calculated for the respective partial regions, the control function 351 displays, as illustrated in FIG. 7B, a color image in which regions corresponding to a plurality of ranges of the coronary artery on a volume-rendered image of the coronary artery are represented in certain colors corresponding to values of the capillary resistance indices. In this case, the image generation function 353 generates the volume-rendered image of the coronary artery from the acquired CT image data, for example. The control function 351 displays the color image in which the regions of the coronary artery in the generated volume-rendered image are represented in certain colors corresponding to the values of the capillary resistance indices.

Here, if a range including a plurality of partial regions is adopted as a target (for example, if the range including the partial region R411 and the partial region R412 in FIG. 5A is adopted as a target), a value of a capillary resistance index to be assigned to a region of the coronary artery in this range (for example, the region from the position P1 to the position P61 in FIG. 5A) may be an average of capillary resistance indices in the respective partial regions or the smallest capillary resistance index among the capillary resistance indices in the partial regions.

Further, if a plurality of capillary resistance indices are finely calculated along the coronary artery in accordance with division into smaller parts, the control function 351 is able to display a graph representing the capillary resistance index at each of positions in the coronary artery. For example, the control function 351 performs control of displaying a display image in which the coronary artery is represented on a two-dimensional plane along a long-axis direction and a graph that represents a change of the indices calculated for the respective ranges of the coronary artery such that positions in the display image and positions in the graph are associated with one another.

Figure 8A:
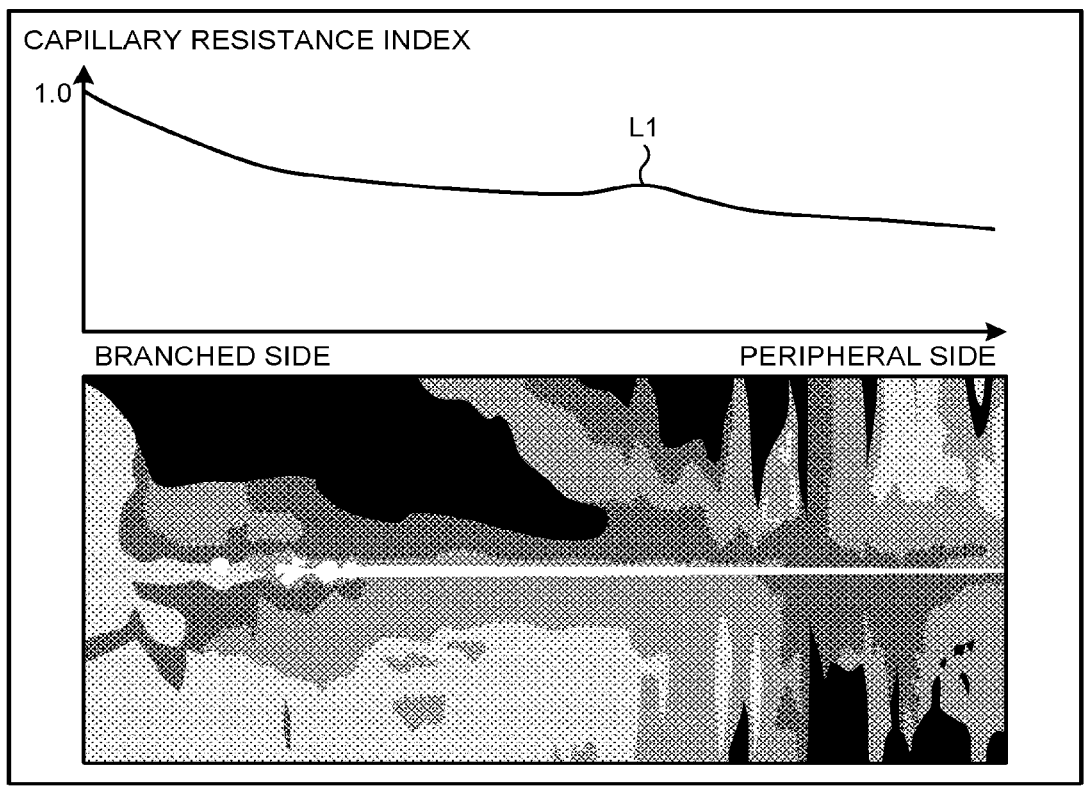
FIG. 8A is a diagram illustrating an example of a display mode of the capillary resistance index according to the first embodiment.

As one example, as illustrated in FIG. 8A, the control function 351 displays a graph in which the vertical axis represents the capillary resistance index and the horizontal axis represents the position in the coronary artery. Further, the control function 351 displays an SPR image of the coronary artery at the same positions as those on the horizontal axis, in association with the graph. In this case, the image generation function 353 generates, from the CT image data, the SPR image of the coronary artery for which the capillary resistance indices have been calculated, for example. Furthermore, the image generation function 353 generates the graph of the capillary resistance index on a scale on which the positions in the coronary artery in the generated SPR image and the positions on the horizontal axis of the graph are associated with one another. The control function 351 displays the graph and the SPR image generated by the image generation function 353 in an associated manner as illustrated in FIG. 8A.

Figure 8B:
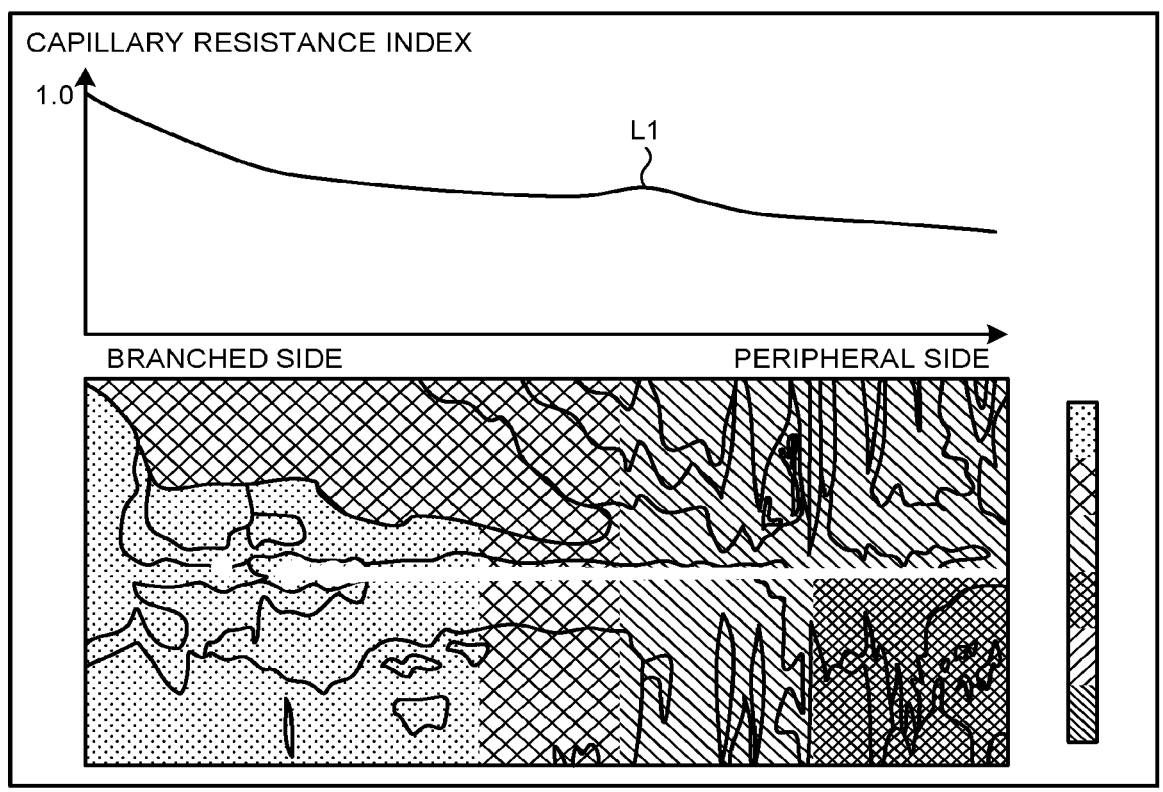
FIG. 8B is a diagram illustrating an example of a display mode of the capillary resistance index according to the first embodiment.

Moreover the control function 351 is further able to perform control of displaying a result of myocardial perfusion in the display image. For example, as illustrated in FIG. 8B, the control function 351 displays a color image in which a myocardial region in the SPR image is represented in certain colors corresponding to results of myocardial blood flow volumes calculated by the acquisition function 352.

Figure 9:
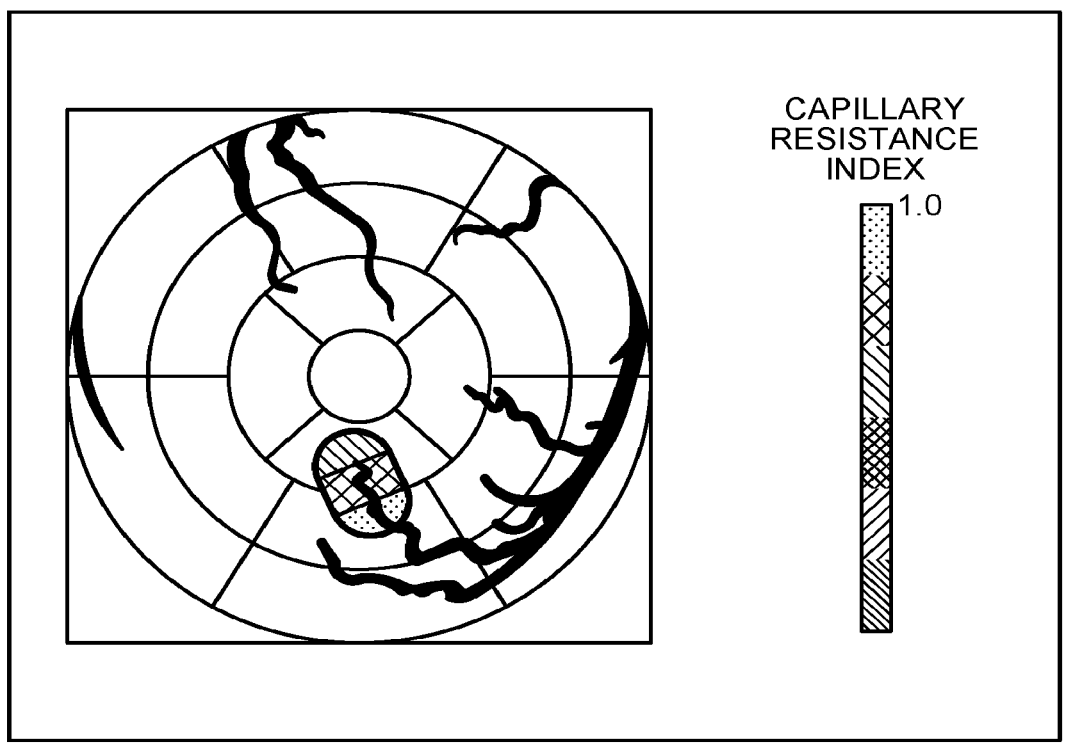
FIG. 9 is a diagram illustrating an example of a display mode of the capillary resistance index according to the first embodiment.

Furthermore, the medical information processing apparatus 300 is able to use a polar map to display the entire myocardium. For example, the control function 351 performs control of displaying a color image in which the coronary artery and the myocardial region are displayed in a distinguishable manner and indices calculated for respective divided ranges are represented in certain colors on a display image in which a myocardium is displayed in polar coordinates. As one example, as illustrated in FIG. 9, the control function 351 displays a display image in which the coronary artery and the target region for which the capillary resistance indices have been calculated are superimposed on the polar map in which the entire myocardium is displayed in polar coordinates.

In this case, the image generation function 353 generates an image of the coronary artery and an image of the target region in shapes corresponding to positions on the polar map. Then, the control function 351 displays the generated image of the coronary artery and the generated image of the target region at corresponding positions on the polar map in a superimposed manner. In this case, as illustrated in FIG. 9, the control function 351 displays the color image by representing each of partial regions in the target region in a certain color corresponding to a value of the capillary resistance index calculated by the calculation function 354.

As described above, the control function 351 is able to display the capillary resistance index in various display modes. Here, the control function 351 is able to perform display by appropriately combining the display images of the various modes as described above. For example, the control function 351 is able to display, side by side, all of the display images as illustrated in FIG. 6 to FIG. 9, or display, side by side, a plurality of display images selected from among all of the display images.

If the control function 351 displays a plurality of display images side by side, the control function 351 is able to display markers indicating positional relationships among the images. For example, when displaying, side by side, the color image, a combination of the graph and the SPR image, the polar map, and the like, the control function 351 arranges and displays markers indicating an approximately identical position on the images.

Figure 10:
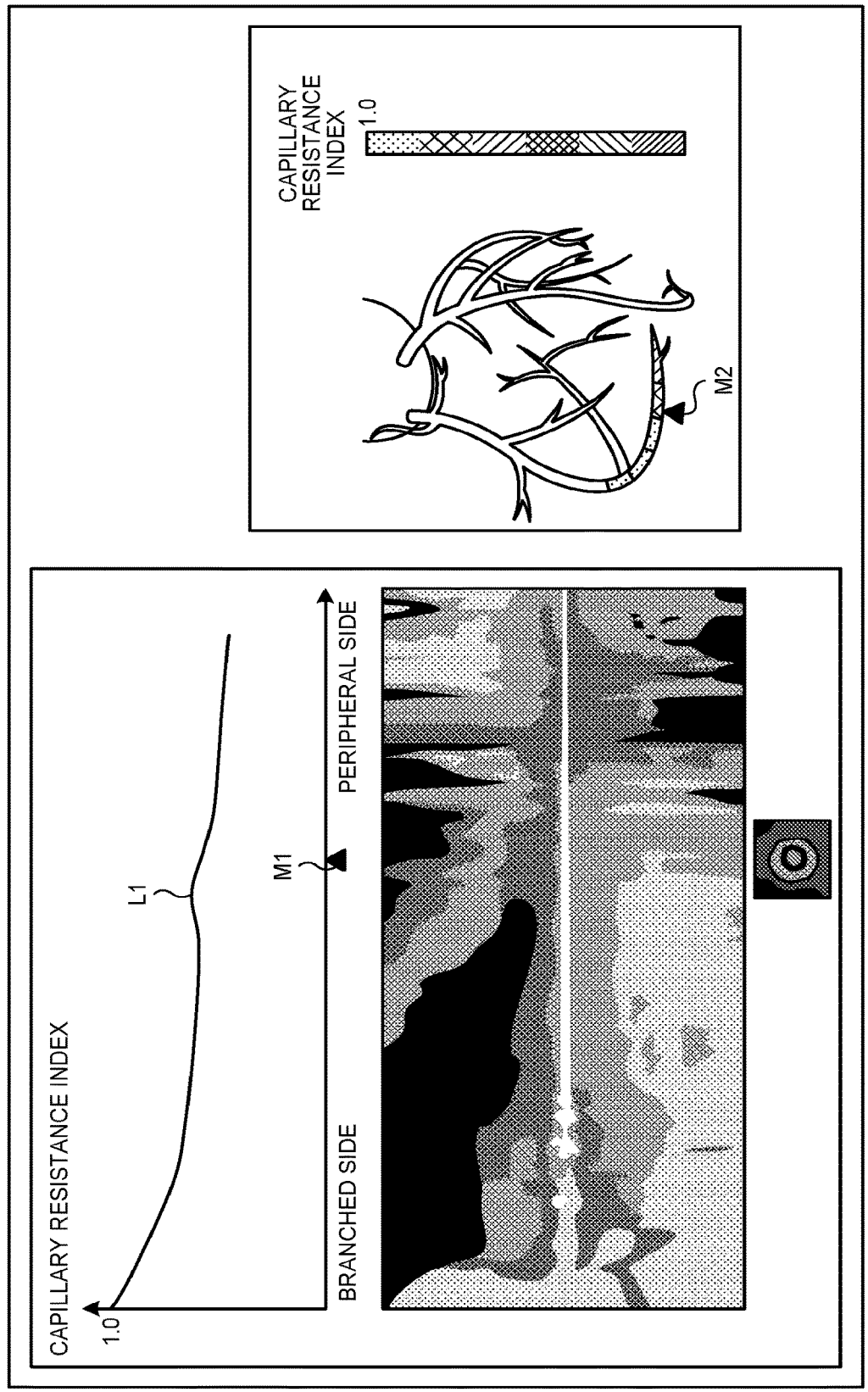
FIG. 10 is a diagram illustrating an example of a display mode of the capillary resistance index according to the first embodiment.

As one example, as illustrated in FIG. 10, when displaying a combination of the graph in which the vertical axis represents the capillary resistance index and the horizontal axis represents the position of the coronary artery and the SPR image of the coronary artery at the same positions as those on the horizontal axis, and displaying the color image based on the volume-rendered image of the coronary artery, the control function 351 displays a marker M1 and a marker M2 indicating an approximately identical position on the coronary artery.

In other words, the control function 351 acquires information on a positional relationship between positions on the horizontal axis of the graph (the SPR image) and positions in the coronary artery in the volume-rendered image, on the basis of coordinate information that is obtained when the image generation function 353 generates the SPR image and the volume-rendered image. Then, the control function 351 arranges the marker M1 indicating an approximately identical position in the coronary artery on the horizontal axis of the graph (or the SPR image), and arranges the marker M2 beside the coronary artery in the volume-rendered image, on the basis of the acquired information on the positional relationship.

In this case, display of the markers may be started at the same time the plurality of display images are displayed, or may be started in accordance with a marker display start instruction that is issued by the operator via the input interface 330. Further, the markers are moved in accordance with a movement instruction that is issued by the operator via the input interface 330. In other words, the control function 351 moves and displays the markers at positions corresponding to marker moving operation that is performed via the input interface 330. At this time, the control function 351 moves the plurality of markers arranged in the plurality of display images in a synchronous manner. For example, when the operator performs operation of moving the marker M1, the control function 351 moves the marker M2 in a synchronous manner.

Furthermore, the control function 351 is also able to display a short-axis cross-sectional image of the coronary artery at a designated position. For example, when arranging a marker with respect to the coronary artery, the control function 351 performs control of further displaying a short-axis cross-sectional image of the coronary artery at the arranged position. As one example, as illustrated in FIG. 10, if the marker M1 is arranged with respect to the coronary artery, the image generation function 353 first generates a cross-cut image (a cross-sectional image perpendicular to the centerline) at the position at which the marker M1 is arranged. The control function 351 displays the generated short-axis cross-sectional image at a position corresponding to the marker M1 on the horizontal axis of the SPR image (or the graph).

In the above-described example, the case has been described in which the capillary resistance index is displayed in various display modes. However, the medical information processing apparatus 300 is further able to display an index value other than the capillary resistance index.

Figure 11:
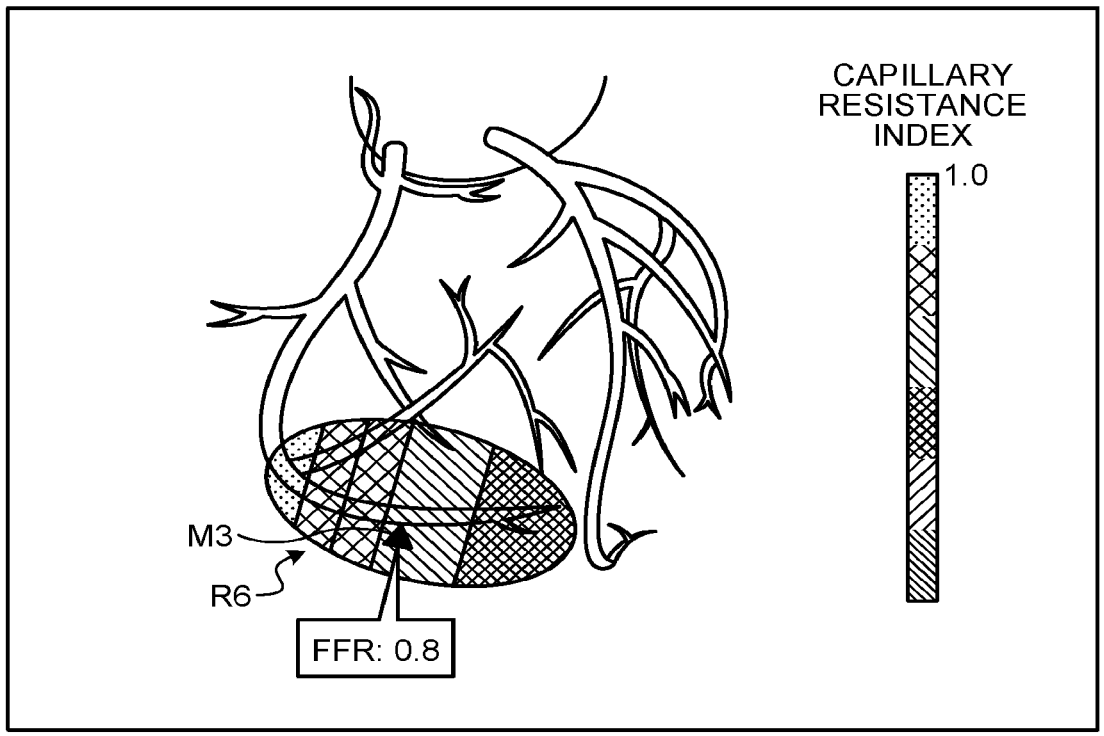
FIG. 11 is a diagram illustrating an example of a display mode of the capillary resistance index according to the first embodiment.

For example, the control function 351 performs control of displaying, in a superimposed manner, a three-dimensional image of the coronary artery and a color image in which indices of respective ranges are represented in certain colors on a three-dimensional image of the myocardial region, and further displaying a marker indicating a position in the coronary artery and fractional flow reserve (FFR) at the position of the marker. As one example, as illustrated in FIG. 11, the control function 351 displays a marker M3 in a superimposed image in which a volume-rendered image of the coronary artery and a volume-rendered image of a region R6 for which a capillary resistance index has been calculated are superimposed. Then, the control function 351 further displays "0.8" as a value of FFR at the marker M3.

In other words, the control function 351 acquires the value of FFR at the position of the marker M3 from a result of fluid analysis performed by the acquisition function 352, and displays the value at the position of the marker M3 in the superimposed image. Here, the position of the marker M3 is moved by moving operation that is performed by the operator via the input interface 330. The control function 351 acquires the value of FFR at the position of the moved marker M3 and displays the value at the position of the marker M3 in the superimposed image, every time the marker M3 is moved by the moving operation.

Figure 12:
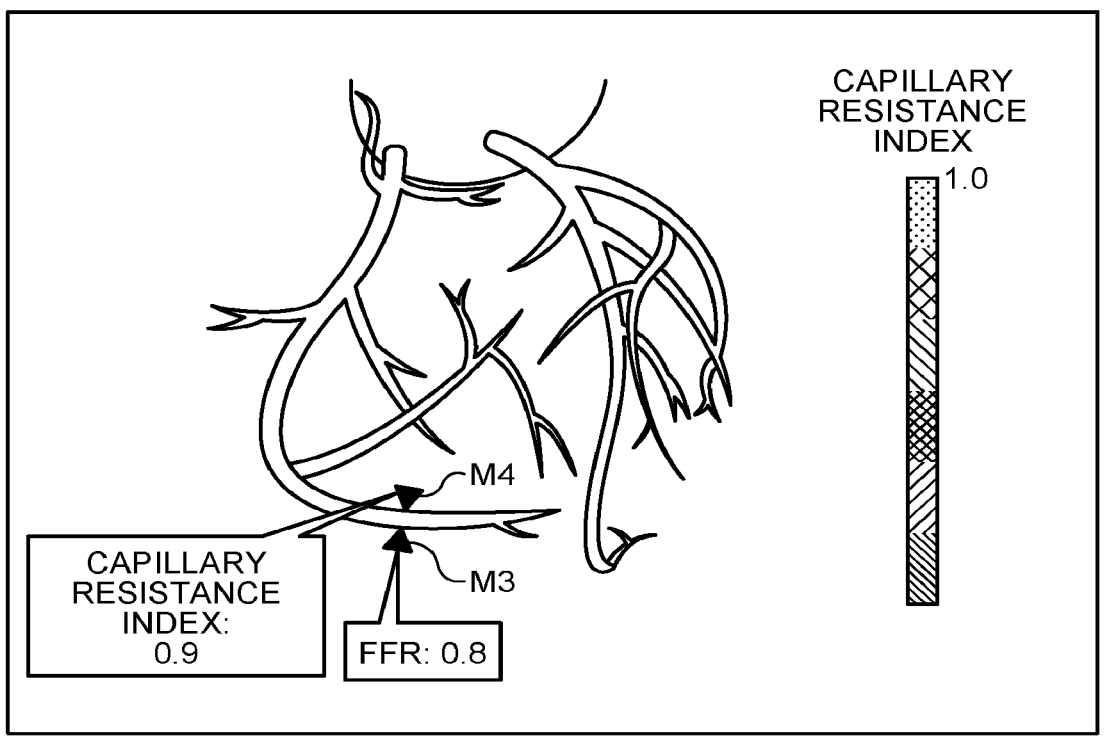
FIG. 12 is a diagram illustrating an example of a display mode of the capillary resistance index according to the first embodiment.

Furthermore, for example, the control function 351 performs control of displaying a three-dimensional image of the coronary artery, a marker indicating a position in the coronary artery, a capillary resistance index at the position of the marker, and fractional flow reserve at the position of the marker. As one example, as illustrated in FIG. 12, the control function 351 displays the marker M3 and a marker M4 in a volume-rendered image of the coronary artery. Then, the control function 351 further displays "0.8" as the value of FFR at the marker M3 and "0.9" as the value of the capillary resistance index at the marker M4.

Here, the positions of the marker M3 and the marker M4 are moved by the moving operation that is performed by the operator via the input interface 330. The control function 351 acquires the value of FFR at the position of the moved marker M3 and displays the value at the position of the marker M3 in the volume-rendered image, every time the marker M3 is moved by the moving operation. Further, the control function 351 acquires the value of the capillary resistance index at the position of the moved marker M4 and displays the value at the position of the marker M4 in the volume-rendered image, every time the marker M4 is moved by the moving operation. Meanwhile, the marker M3 and the marker M4 may be controlled such that one of the markers moves in synchronization with the moving operation that is performed on the other one of the markers. In other words, the marker M3 and the marker M4 may be moved independently of each other or in synchronization with each other.

Figure 13:
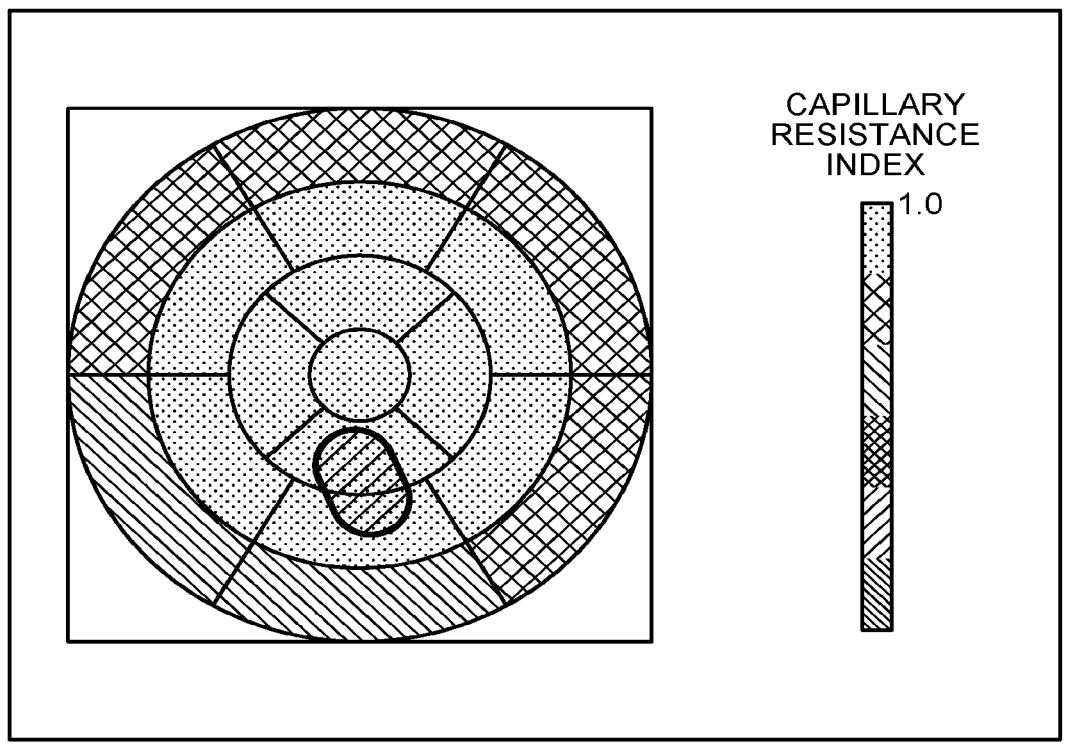
FIG. 13 is a diagram illustrating an example of a display mode of the capillary resistance index according to the first embodiment.

Moreover, for example, the control function 351 performs control of displaying a result of myocardial perfusion on a display image in which the myocardium is displayed in polar coordinates, and displaying, in a distinguishable manner, a region in which the capillary resistance index is smaller than a threshold in a myocardial region included in the display image. As one example, as illustrated in FIG. 13, the control function 351 assigns, to the polar map, certain colors corresponding to values of myocardial blood flow volumes that are obtained through the myocardial perfusion, and further displays the region for which the capillary resistance index is smaller than the threshold in a distinguishable manner. In this case, for example, the control function 351 displays the region for which the index is smaller than the threshold in a distinguishable manner by enclosing the region in a frame or masking the region in a different color.

Figure 14:
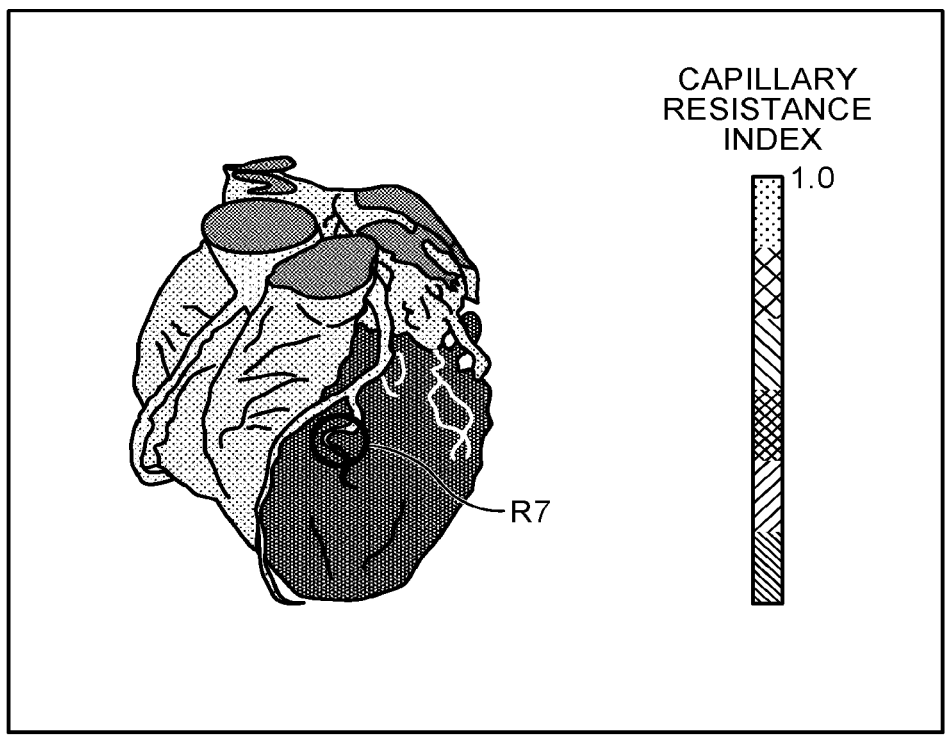
FIG. 14 is a diagram illustrating an example of a display mode of the capillary resistance index according to the first embodiment.

Furthermore, for example, the control function 351 performs control of displaying a result of myocardial perfusion on a three-dimensional image of the myocardium, and displaying, in a distinguishable manner, a region in which the index is smaller than a threshold in a myocardial region included in the three-dimensional image. As one example, as illustrated in FIG. 14, the control function 351 assigns, to the polar map, certain colors corresponding to values of myocardial blood flow volumes that are obtained through the myocardial perfusion, and further displays the region for which the capillary resistance index is smaller than the threshold in a distinguishable manner. In this case, for example, the control function 351 displays the region for which the index is smaller than the threshold in a distinguishable manner by enclosing the region in a frame or masking the region in a different color.

Moreover, for example, the control function 351 performs control of displaying a three-dimensional image of the coronary artery, and when receiving designation operation of designating a position in the coronary artery in the three-dimensional image, performs control of displaying, side by side, fractional flow reserve at the received position, a result of myocardial perfusion in a myocardial region to which the coronary artery at the received position supplies blood, a capillary resistance index at the received position, and a value based on a pixel value at the received position. In other words, the control function 351 is able to simultaneously display various indices when a position is designated on the coronary artery.

Figure 15:
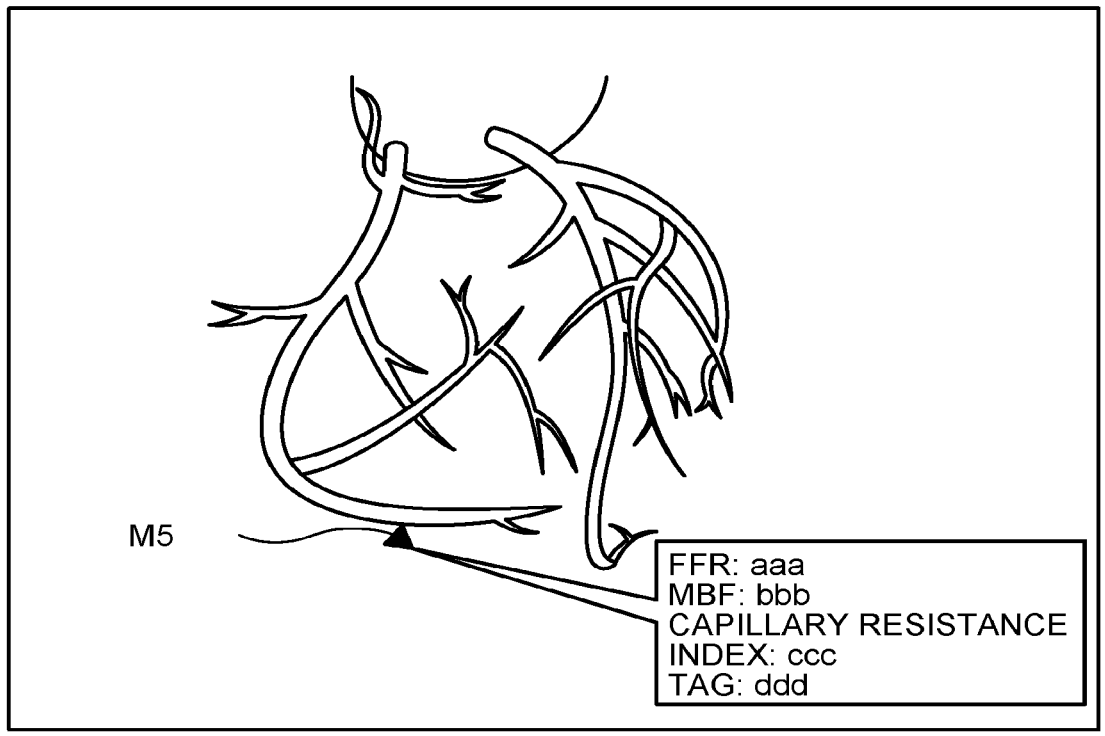
FIG. 15 is a diagram illustrating an example of a display mode of the capillary resistance index according to the first embodiment.

As one example, as illustrated in FIG. 15, the control function 351 arranges and displays a marker M5 for designating a position in a coronary artery among coronary arteries in a volume-rendered image of the coronary arteries. Then, the control function 351 displays, side by side, "FFR: aaa", "MBF: bbb", "capillary resistance index: ccc" and "TAG: ddd" at the position of the marker M5.

Meanwhile, MBF stands for myocardial blood flow that means the myocardial blood flow volume, and the myocardial blood flow volume in a myocardium adjacent to the position of the marker M5 is displayed. Further, TAG stands for transluminal attenuation gradient that is the value based on the pixel value (HU value) in the coronary artery, and represents a tilt (a spatial change rate of the HU value) in a graph in which the horizontal axis represents a distance from an upstream side to a downstream side along the centerline of the coronary artery and the vertical axis represents the HU value at each of distances.

For example, when a contrast agent is introduced and transferred a certain distance between two points in the coronary artery, it takes a longer time as the blood flow decreases, so that a difference in a contrast effect increases in a blood vessel in which the blood flow decreases due to a lesion, and TAG increases as the blood flow decreases. Meanwhile, TAG is calculated by the acquisition function 352 by using the coronary angiography CT image data.

Furthermore, for example, the control function 351 performs control of displaying a three-dimensional image of a myocardium, and when receiving designation operation of designating a myocardial region in the three-dimensional image, performs control of displaying, side by side, fractional flow reserve in a coronary artery that supplies blood to the received myocardial region, a result of myocardial perfusion in the received myocardial region, and the capillary resistance index in the received myocardial region.

Figure 16:
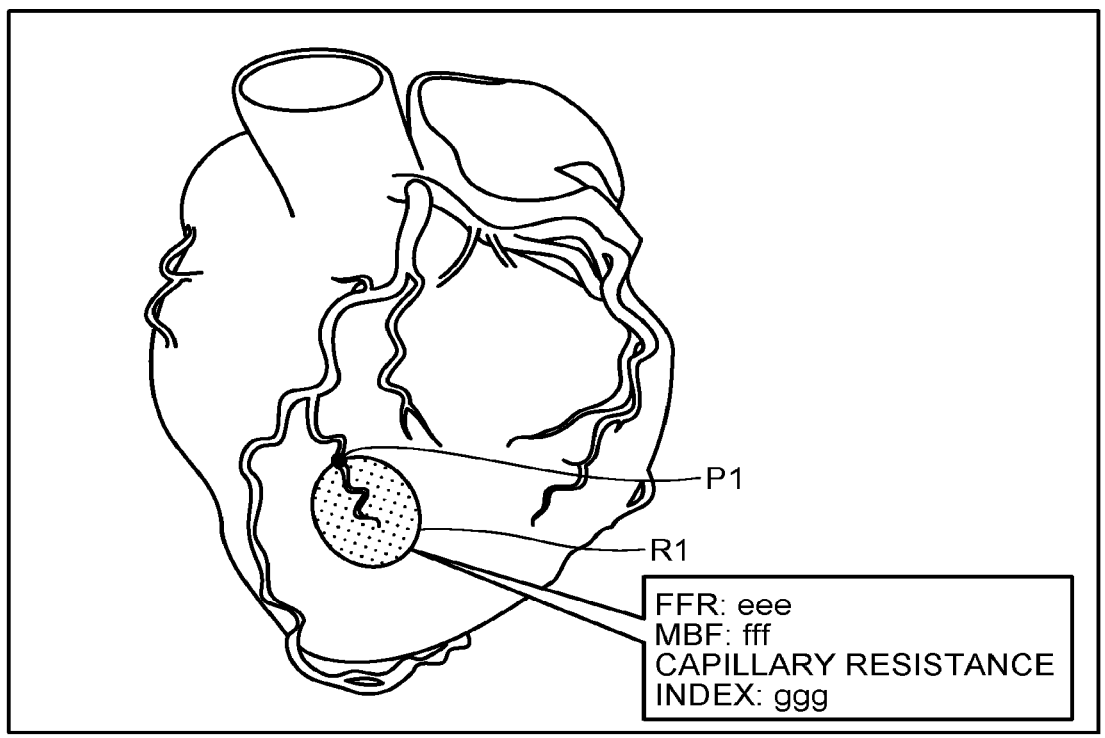
FIG. 16 is a diagram illustrating an example of a display mode of the capillary resistance index according to the first embodiment.

As one example, as illustrated in FIG. 16, if the region R1 for calculating the capillary resistance index is designated with respect to a myocardium in a volume-rendered image of a heart, the control function 351 displays, side by side, "FFR: eee" at the position P1 in the coronary artery that supplies blood to the region R1, "MBF: fff" in the region R1, and "capillary resistance index: ggg" in the region R1.

Moreover, for example, the control function 351 displays a recommended therapeutic strategy for at least one of the received position and the received myocardial region, on the basis of a result of comparison between each of display items that are displayed side by side and a threshold that is set for each of the display items. For example, when a plurality of display items (FFR, MBF, and the like) are displayed side by side as illustrated in FIG. 15 and FIG. 16, the control function 351 is able to display a recommended therapeutic strategy.

In this case, first, the determination function 355 determines a recommended therapeutic strategy by comparing each of the display items with a corresponding threshold. For example, the determination function 355 determines a recommended therapeutic strategy on the basis of determination criteria as illustrated in FIG. 17. FIG. 17 is a diagram for explaining an example of the determination criteria for determining a therapeutic strategy according to the first embodiment. In FIG. 17, determination criteria used to determine a therapeutic strategy using FFR, MBF, and the capillary resistance index are illustrated. Further, in FIG. 17, an upward arrow (↑) indicates that a value is higher than a threshold, and a downward arrow (↓) indicates that a value is lower than the threshold.

The determination criteria as illustrated in FIG. 17 are set and stored in the memory 320 in advance. In other words, the determination function 355 performs determination with reference to the determination criteria stored in the memory 320 when performing the determination. Further, each of the thresholds used for the determination on each of the display items is set in advance by the operator or the like.

For example, as illustrated in FIG. 17, in the case of "FFR: ↓, MBF: ↓, capillary resistance index: ↑", the determination function 355 determines "catheter treatment" as a "recommended treatment". Further, as illustrated in FIG. 17, in the case of "FFR: ↑, MBF: ↓, capillary resistance index: ↓", the determination function 355 determines "drug treatment" as the "recommended treatment". Furthermore, as illustrated in FIG. 17, in the case of "FFR: ↓, MBF: ↑, capillary resistance index: ↑", the determination function 355 determines "treatment is not needed" as the "recommended treatment". Moreover, as illustrated in FIG. 17, in the case of "FFR: ↓, MBF: ↓, capillary resistance index: ↓", the determination function 355 determines "catheter treatment" and "drug treatment" as the "recommended treatment".

The control function 351 displays a result (recommended treatment) determined by the determination function 355, in association with each of the display items in the display image. The determination of the recommended treatment as described above may be performed for each of positions of coronary arteries or for each of myocardial regions. In other words, every time the operator moves the marker M5 or designates a target region for calculating the capillary resistance index by using the input interface 330, the determination function 355 determines a recommended therapeutic strategy at each of moved positions and the control function 351 displays a determination result.

Meanwhile, the determination criteria as illustrated in FIG. 17 are one example, and embodiments are not limited thereto. For example, it may be possible to use TAG or other indices as items to be compared with thresholds.

Figure 18:
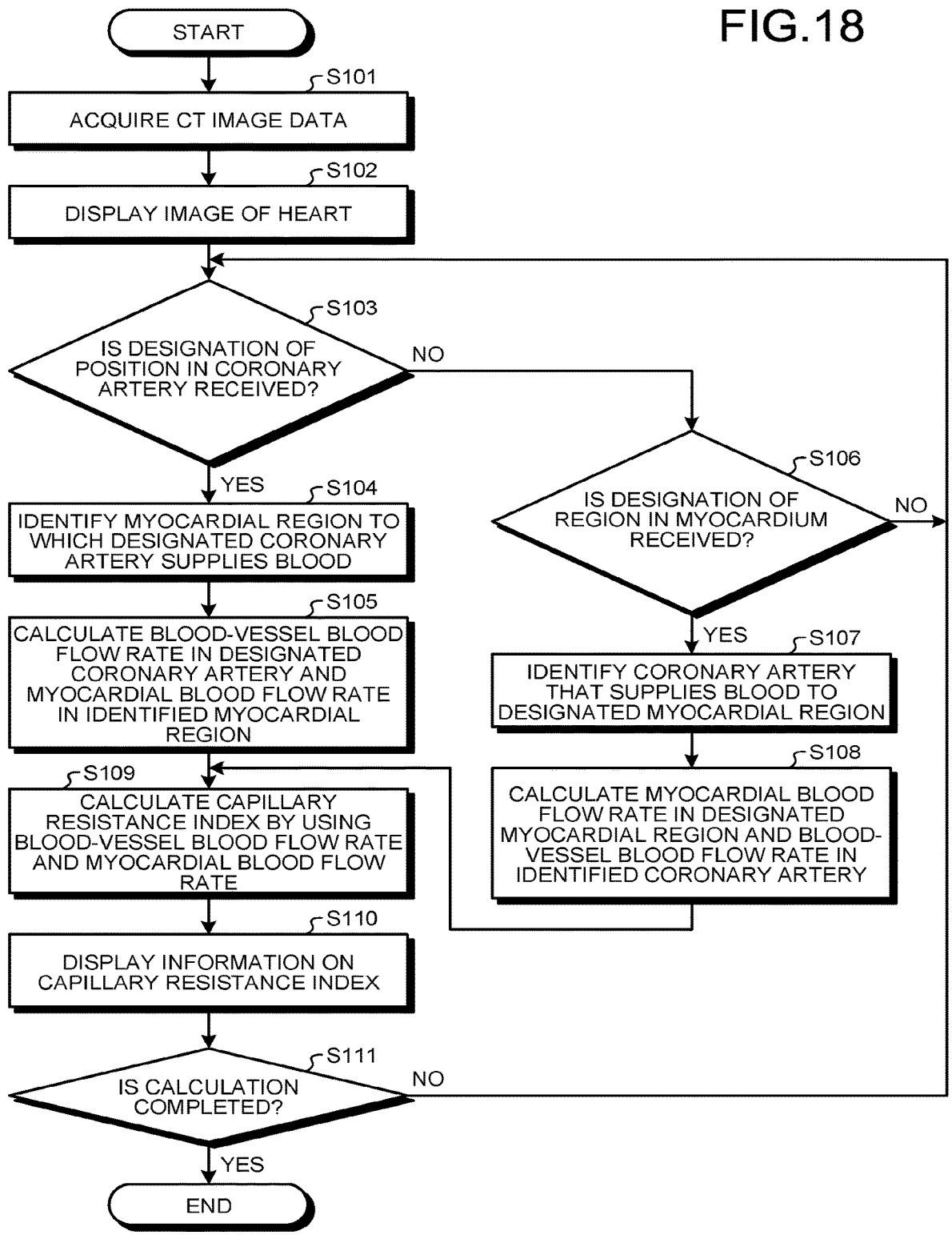
FIG. 18 is a flowchart illustrating the flow of processing performed by the medical information processing apparatus according to the first embodiment.

Next, the flow of processing performed by the medical information processing apparatus 300 according to the first embodiment will be described. FIG. 18 is a flowchart illustrating the flow of the processing performed by the medical information processing apparatus 300 according to the first embodiment. Here, Step S101 and Step S111 in FIG. 18 are realized by causing the processing circuitry 350 to read a program corresponding to the control function 351 from the memory 320 and execute the program, for example. Further, Step S103 to Step S108 are realized by causing the processing circuitry 350 to read a program corresponding to the acquisition function 352 from the memory 320 and execute the program, for example. Furthermore, Step S109 is realized by causing the processing circuitry 350 to read a program corresponding to the calculation function 354 from the memory 320 and execute the program, for example. Moreover, Step S102 and Step S110 are realized by causing the processing circuitry 350 to read a program corresponding to the control function 351 and the image generation function 353 from the memory 320 and execute the program, for example.

In the medical information processing apparatus 300 according to the present embodiment, first, the processing circuitry 350 acquires CT image data (Step S101). Subsequently, the processing circuitry 350 generates an image of the heart from the CT image data and displays the image (Step S102). Then, the processing circuitry 350 determines whether designation of a position in a coronary artery is received (Step S103). If designation of a position in the coronary artery is received (Yes at Step S103), the processing circuitry 350 identifies a myocardial region to which the designated coronary artery supplies blood (Step S104), and calculates a blood-vessel blood flow volume in the designated coronary artery and a myocardial blood flow volume in the identified myocardial region (Step S105).

In contrast, at Step S103, if designation of a position in the coronary artery is not received (No at Step S103), the processing circuitry 350 determines whether designation of a region in a myocardium is received (Step S106). If designation of a region in the myocardium is received (Yes at Step S106), the processing circuitry 350 identifies a coronary artery that supplies blood to the designated myocardial region (Step S107), and calculates a myocardial blood flow volume in the designated myocardial region and a blood-vessel blood flow volume in the identified coronary artery (Step S108). At Step S106, if designation of a region in the myocardium is not received (No at Step S106), the processing circuitry 350 returns to Step S103, and continues to perform determination.

At Step S105 or Step S108, if the blood-vessel blood flow volume and the myocardial blood flow volume are calculated, the processing circuitry 350 calculates a capillary resistance index by using the blood-vessel blood flow volume and the myocardial blood flow volume (Step S109). Then, the processing circuitry 350 generates information on the calculated capillary resistance index and displays the information (Step S110). Thereafter, the processing circuitry 350 determines whether calculation of the capillary resistance index is completed (Step S111), and if the calculation is completed (Yes at Step S111), terminates the processing. In contrast, if the calculation is not completed (No at Step S111), the processing circuitry 350 returns to Step S103, and continues to perform determination.

As described above, according to the first embodiment, the acquisition function 352 acquires the blood-vessel blood flow volume in the coronary artery and the myocardial blood flow volume in the myocardial region to which the coronary artery supplies blood. The calculation function 354 calculates an index indicating an amount of capillary resistance in a capillary that supplies blood to the myocardial region, by combining the blood-vessel blood flow volume and the myocardial blood flow volume. Therefore, the medical information processing apparatus 300 according to the first embodiment is able to calculate a capability to supply blood from the coronary artery to the myocardial region (a degree of blood flow inhibition in a capillary between the coronary artery and the myocardium), and able to provide an index by which resistance in the capillary can be evaluated.

For example, coronary flow reserve (CFR) has been known as an index for making a diagnosis of myocardial ischemia. The capillary resistance index according to the present application has the same clinical implication as CFR. However, CFR is a ratio of a myocardial blood flow volume in a stressed state and a myocardial blood flow volume in a resting state; therefore, to calculate the myocardial blood flow volumes from the CT image data, it is necessary to perform imaging twice in the stressed state and the resting state, so that radiation exposure increases. Further, to calculate CFR, vasodilator is used to cause a blood vessel to be in the stressed state, so that a burden on the subject increases.

In contrast, the capillary resistance index according to the present application can be calculated by obtaining CT image data of a plurality of heartbeats in a plurality of time phases, so that it is possible to reduce radiation dose. Further, the capillary resistance index according to the present application can be calculated in the resting state, so that it is possible to reduce a burden of drug administration on the subject. In other words, the capillary resistance index according to the present application can be calculated for a subject for whom vasodilator administration is not suitable.

Furthermore, the capillary resistance index according to the present application uses the blood-vessel blood flow volume in the coronary artery and the myocardial blood flow volume that can be calculated by various methods, so that the index can be calculated for various subjects.

Moreover, according to the first embodiment, the acquisition function 352 acquires a plurality of blood-vessel blood flow volumes in a plurality of coronary arteries and a single myocardial blood flow volume in which a plurality of myocardial blood flow volumes in a plurality of myocardial regions to which the respective coronary arteries supply blood are combined. The calculation function 354 calculates the capillary resistance index by combining the plurality of blood-vessel blood flow volumes and the single myocardial blood flow volume. Therefore, the medical information processing apparatus 300 according to the first embodiment is able to provide the capillary resistance index that accurately reflects blood supply from the coronary artery to the myocardium.

Furthermore, according to the first embodiment, the acquisition function 352 acquires a blood-vessel blood flow volume in an end portion on an upstream side and a blood-vessel blood flow volume in an end portion on a downstream side of a certain range of the coronary artery that supplies blood to the myocardial region, and acquires a myocardial blood flow volume in the designated myocardial region. The calculation function 354 calculates a capillary resistance index by combining a difference between the blood-vessel blood flow volume in the end portion on the upstream side and the blood-vessel blood flow volume in the end portion on the downstream side and the myocardial blood flow volume in the designated myocardial region. Therefore, the medical information processing apparatus 300 according to the first embodiment is able to provide the capillary resistance index with high accuracy.

Moreover, according to the first embodiment, the acquisition function 352 divides the coronary artery and the myocardial region to which the coronary artery supplies blood into a plurality of ranges, and acquires, for each of the divided ranges, a blood-vessel blood flow volume in an end portion on an upstream side and a blood-vessel blood flow volume in an end portion on a downstream side of each of the ranges and a myocardial blood flow volume in a myocardial region corresponding to each of the ranges. The calculation function 354 calculates a capillary resistance index for each of the divided ranges by combining a difference between the blood-vessel blood flow volume in the end portion on the upstream side and the blood-vessel blood flow volume in the end portion on the downstream side and the myocardial blood flow volume in the myocardial region corresponding to each of the ranges. Therefore, the medical information processing apparatus 300 according to the first embodiment is able to provide the capillary resistance index for a smaller region.

Furthermore, according to the first embodiment, the control function 351 performs control of displaying a display image indicating information on the capillary resistance index calculated by the calculation function 354, on a medical image that includes at least one of the myocardial region and the coronary artery. Therefore, the medical information processing apparatus 300 according to the first embodiment is able to provide more easily understandable information on the capillary resistance index.

Moreover, according to the first embodiment, the control function 351 performs control of displaying a color image in which capillary resistance indices calculated for the respective divided ranges are represented in certain colors and allocated on a three-dimensional image of the myocardial region or the coronary artery. Therefore, the medical information processing apparatus 300 according to the first embodiment is able to provide more easily understandable information on the capillary resistance index in each of the regions.

Furthermore, according to the first embodiment, the control function 351 performs control of displaying a display image in which the coronary artery is represented on a two-dimensional plane along a long-axis direction and a graph that represents a change of the capillary resistance indices calculated for the respective ranges of the coronary artery such that positions in the display image and positions in the graph are associated with one another. Therefore, the medical information processing apparatus 300 according to the first embodiment is able to display a relationship between the property of the myocardium and the capillary resistance index in a more easily understandable manner.

Moreover, according to the first embodiment, the control function 351 performs control of displaying a result of myocardial perfusion in the display image. Therefore, the medical information processing apparatus 300 according to the first embodiment is able to provide more easily understandable information on a relationship between the myocardial blood flow volume and the capillary resistance index.

Furthermore, according to the first embodiment, the control function 351 performs control of displaying a color image in which the coronary artery and the myocardial region are displayed in a distinguishable manner and indices calculated for respective divided ranges are represented in certain colors on a display image in which a myocardium is displayed in polar coordinates. Therefore, the medical information processing apparatus 300 according to the first embodiment is able to provide more easily understandable information on the capillary resistance index in the target region while allowing the entire myocardium to be recognized.

Moreover, according to the first embodiment, the control function 351 performs control of displaying at least two of a first color image in which capillary resistance indices calculated for the respective divided ranges are represented in certain colors and allocated on a three-dimensional image of the myocardial region or the coronary artery, a combination of a display image in which the coronary artery is represented on a two-dimensional plane along a long-axis direction and a graph that represents a change of the capillary resistance indices calculated for the respective ranges of the coronary artery, and a second color image in which the coronary artery and the myocardial region are displayed in a distinguishable manner and the capillary resistance indices calculated for a plurality of divided ranges are represented in certain colors on a display image in which the myocardium is displayed in polar coordinates. Furthermore, the control function 351 performs control of arranging and displaying markers indicating an approximately identical position on at least the displayed two of the first color image, the combination of the display image and the graph, and the second color image. Therefore, the medical information processing apparatus 300 according to the first embodiment is able to make a diagnosis by comparing a plurality of display images and clarify positional relationships among the plurality of images. Moreover, it is possible to perform observation by comparing morphologies of the myocardium and morphology of the coronary artery and the capillary resistance index, so that it is possible to assess ischemia and myocardial infraction and determine a therapeutic strategy.

Furthermore, according to the first embodiment, when the marker is arranged with respect to the coronary artery, the control function 351 performs control of further displaying a short-axis cross-sectional image of the coronary artery at the arranged position. Therefore, the medical information processing apparatus 300 according to the first embodiment is able to provide more detailed morphological information.

Moreover, according to the first embodiment, the control function 351 performs control of further displaying, in a superimposed manner, a three-dimensional image of the coronary artery and a color image in which capillary resistance indices of respective ranges are represented in certain colors on a three-dimensional image of the myocardial region, and further displaying a marker indicating a position in the coronary artery and fractional flow reserve at the position of the marker. Therefore, the medical information processing apparatus 300 according to the first embodiment is able to perform observation by comparing the capillary resistance index and a value of FFR.

Furthermore, according to the first embodiment, the control function 351 performs control of displaying a three-dimensional image of the coronary artery, a marker indicating a position in the coronary artery, a capillary resistance index at the position of the marker, and fractional flow reserve at the position of the marker. Therefore, the medical information processing apparatus 300 according to the first embodiment is able to perform observation by comparing the capillary resistance index and a value of FFR.

Moreover, according to the first embodiment, the control function 351 performs control of displaying a result of myocardial perfusion on a display image in which a myocardium is displayed in polar coordinates, and displaying, in a distinguishable manner, a region in which the capillary resistance index is smaller than a threshold in a myocardial region included in the display image. In addition, the control function 351 performs control of displaying a result of myocardial perfusion on a three-dimensional image of a myocardium, and displaying, in a distinguishable manner, a region in which the capillary resistance index is smaller than a threshold in a myocardial regions included in the three-dimensional image. Therefore, the medical information processing apparatus 300 according to the first embodiment is able to perform observation by comparing a result of the myocardial blood flow volume and the capillary resistance index, so that it is possible to identify a myocardial region that is recovered by reperfusion, and determine a therapeutic strategy.

Furthermore, according to the first embodiment, the control function 351 performs control of displaying a three-dimensional image of the coronary artery, and when receiving designation operation of designating a position in the coronary artery in the three-dimensional image, performs control of displaying, side by side, fractional flow reserve at the received position, a result of myocardial perfusion in a myocardial region to which the coronary artery at the received position supplies blood, the capillary resistance index at the received position, and a value based on a pixel value at the received position. In addition, the control function 351 performs control of displaying a three-dimensional image of a myocardium, and when receiving designation operation of designating a myocardial region in the three-dimensional image, performs control of displaying, side by side, fractional flow reserve in a coronary artery that supplies blood to the received myocardial region, a result of myocardial perfusion in the received myocardial region, and an index in the received myocardial region. Therefore, the medical information processing apparatus 300 according to the first embodiment is able to identify a cause of ischemia that can hardly be determined based on only a specific index, and able to determine a therapeutic strategy.

Moreover, according to the first embodiment, the control function 351 displays a recommended therapeutic strategy for at least one of the received position and the received myocardial region, on the basis of a result of comparison between each of display items that are displayed side by side and a threshold that is set for each of the display items. Therefore, the medical information processing apparatus 300 according to the first embodiment is able to support determination of a therapeutic strategy.

Furthermore, according to the first embodiment, the calculation function 354 calculates the capillary resistance index based on a ratio of the blood-vessel blood flow volume and the myocardial blood flow volume. Therefore, the medical information processing apparatus 300 according to the first embodiment is able to easily provide an index for evaluating resistance in a capillary.

Second Embodiment

While the first embodiment has been described above, various other embodiments may be made in addition to the first embodiment as described above.

In the embodiment as described above, the case has been described in which the capillary resistance index is calculated based on a ratio of the blood-vessel blood flow volume and the myocardial blood flow volume. However, embodiments are not limited thereto, and, for example, any calculation using two values, such as calculation of a logarithmic ratio or addition/multiplication of a coefficient with respect to a denominator or a numerator, may be applicable.

As one example, it may be possible to perform multiplication by a blood flow velocity, blood viscosity, an ejection fraction or an ejection amount of the entire heart, or the like as a correction coefficient. In this case, the calculation function 354 acquires information on a flow velocity or viscosity from a result of fluid analysis performed by the acquisition function 352. Further, the calculation function 354 calculates an ejection fraction or an ejection amount of the entire heart on the basis of temporal CT image data that is collected in a plurality of time phases corresponding to one or more heartbeats.

Here, when using a blood flow velocity, for example, the calculation function 354 uses the blood flow velocity as the correction coefficient such that the capillary resistance index is reduced with an increase in the flow velocity. Further, when using blood viscosity, for example, the calculation function 354 uses the blood viscosity as the correction coefficient such that the capillary resistance index is reduced with an increase in the viscosity. Here, if the blood viscosity is used as the correction coefficient, for example, it is possible to further calculate a change in the myocardial blood flow volume in a case where the blood viscosity is reduced due to improvement in lifestyle diseases. In addition, when using the ejection fraction or the ejection amount of the entire heart, for example, the calculation function 354 uses the ejection fraction or the ejection amount of the entire heart as the correction coefficient such that the capillary resistance index periodically changes along with a change in the ejection fraction or the ejection amount of the entire heart.

Moreover, in the embodiment as described above, the case has been described in which information based on the capillary resistance index as it is has been used. However, embodiments are not limited thereto, and, for example, it may be possible to use a value that is obtained by multiplying the capillary resistance index by other coefficients. As one example, the calculation function 354 may display the above-described various kinds of display information by using a value that is obtained by multiplying the calculated capillary resistance index by an index value representing "ease of blood transmission between cells". Accordingly, the medical information processing apparatus 300 is able to provide information indicating a myocardial infraction region and a degree of advancement.

Furthermore, in the embodiment as described above, the case has been described in which a result of myocardial perfusion is used with respect to the SPR image or the polar map. However, embodiments are not limited thereto, and it may be possible to alternatively use a different value that indicates an index of a function of the myocardium. For example, it may be possible to extract local motion in the myocardium by capturing an ultrasound image of the heart, and use the magnitude of the motion rather than the result of the myocardial perfusion.

Moreover, the medical information processing apparatus 300 according to the present application is further able to perform machine learning by using the calculated blood-vessel blood flow volume and the calculated myocardial blood flow volume. For example, the medical information processing apparatus 300 constructs a discriminator by performing machine learning on a relationship among the blood-vessel blood flow volume, the myocardial blood flow volume, and a value of CFR in the target region. The constructed discriminator outputs the value of CFR in response to input of a new blood-vessel blood flow volume and a new myocardial blood flow volume. With this configuration, it is possible to estimate CFR from the blood-vessel blood flow volume and the myocardial blood flow volume. In other words, it is possible to acquire the value of CFR while preventing an increase in radiation dose and administration of vasodilator. Meanwhile, in the above-described machine learning, it may be possible to use a value that is measured through a capillary resistance test, instead of CFR.

Furthermore, in the embodiment as described above, the case has been described in which the blood-vessel blood flow volume and the myocardial blood flow volume are used as the blood-vessel blood flow index and the myocardial blood flow index. However, embodiments are not limited thereto, and it may be possible to use values based on blood pressure as the blood-vessel blood flow index and the myocardial blood flow index.

Moreover, in the embodiment as described above, the case has been described in which an index indicating a capability of blood supply to a myocardial region is calculated by combining the blood-vessel blood flow index and the myocardial blood flow index. However, embodiments are not limited thereto, and it may be possible to calculate an index indicating a capability of blood supply to the myocardial region based on the blood-vessel blood flow index.

In this case, for example, the acquisition function 352 acquires the blood-vessel blood flow index in the coronary artery. As one example, the acquisition function 352 acquires the blood-vessel blood flow volume in the coronary artery by performing fluid analysis on the coronary angiography CT image data that is acquired from the X-ray CT apparatus as the medical image diagnostic apparatus 100 or from the server apparatus 200.

The calculation function 354 calculates an index indicating a capability of blood supply to the myocardial region to which the coronary artery supplies blood, by using an analysis condition on the blood-vessel blood flow index acquired by the acquisition function 352. For example, the calculation function 354 calculates, for each of positions of coronary arteries, an index indicating a capability of blood supply to a control region of the coronary artery on which fluid analysis is performed, by using a parameter (for example, a physical property value of blood, blood vessel shape data, or the like) in the analysis condition for the fluid analysis performed by the acquisition function 352.

In the example as described above, the case has been described in which the acquisition function 352 performs fluid analysis and the calculation function 354 uses an analysis condition for the fluid analysis performed by the acquisition function 352. However, the medical information processing apparatus 300 according to the present application is able to calculate an index by using a result of fluid analysis that is externally performed. In this case, for example, the acquisition function 352 acquires a result of the fluid analysis with parameters of the analysis condition from the server apparatus 200 or the like via the communication interface 310. The calculation function 354 calculates, for each of positions of coronary arteries, an index indicating a capability of blood supply to the control region of the coronary artery on which the fluid analysis has been performed, by using the parameters included in the analysis condition added to a fluid analysis result acquired by the acquisition function 352.

Furthermore, for example, the acquisition function 352 acquires medical image data on which fluid analysis has been performed and a result of the fluid analysis without an analysis condition from the server apparatus 200 or the like via the communication interface 310. The calculation function 354 estimates parameters in the analysis condition for the fluid analysis by using the medical image data and an analytical value. Then, the calculation function 354 calculates, for each of positions of coronary arteries, an index indicating a capability of blood supply to the control region of the coronary artery on which the fluid analysis has been performed, by using the estimated parameters.

Moreover, in the embodiment as described above, the case has been described in which various kinds of processing are performed by the single medical information processing apparatus 300. However, embodiments are not limited thereto, and, for example, the processing circuitry 350 may implement functions by using a processor of an external apparatus that is connected via a network. For example, the processing circuitry 350 implements each of the functions as illustrated in FIG. 1 by reading a program corresponding to each of the functions from the memory 320, executing the programs, and using, as a calculation resource, a server group (cloud) that is connected to the medical information processing apparatus 300 via a network. Furthermore, for example, the memory 320 may be realized by a server group (cloud) that is connected to the medical information processing apparatus 300 via a network.

In the embodiment as described above, the case has been described in which each of processing functions is implemented by a single processing circuitry (the processing circuitry 350), but embodiments are not limited thereto. For example, the processing circuitry 350 may be constructed by a combination of a plurality of independent processors, and may implement each of the processing functions by causing each of the processors to execute each of programs. Further, each of the processing functions included in the processing circuitry 350 may be implemented by appropriately distributing or integrating the functions into a single or a plurality of processing circuitries.

Furthermore, a term "processor" used in the description of each of the embodiments as described above indicates a circuitry, such as a central processing unit (CPU), a graphics processing unit (GPU), an application specific integrated circuit (ASIC), a programmable logic device (for example, a simple programmable logic device (SPLD) or a complex programmable logic device (CPLD)), or a field programmable gate array (FPGA). Here, it may be possible to directly incorporate the programs into a circuitry of the processor, instead of storing the programs in the memory circuitry. In this case, the processor implements the functions by reading the programs incorporated in the circuitry and execute the programs. Moreover, the processors of the embodiment need not always be configured such that each of the processors is constructed as a single circuitry, but may be configured such that a plurality of independent circuitries are combined into a single processor that implements corresponding functions.

Here, the programs executed by the processor are provided by being incorporated in a read only memory (ROM), a memory circuitry, or the like in advance. The programs may be provided by being recorded in a computer-readable storage medium, such as a compact disc-ROM (CD-ROM), a flexible disk (FD), a CD-recordable (CD-R), or a digital versatile disk (DVD), in a computer-installable or a computer-executable file format. Furthermore, the programs may be stored in a computer connected to a network, such as the Internet, and may be provided or distributed by download via the network. For example, the programs may have a module structure including each of functions described above. As actual hardware, the CPU reads the programs from a storage medium, such as a ROM, and executes the programs, so that each of the modules are loaded onto a main storage device and generated on the main storage device.

According to at least one of the embodiments as described above, it is possible to provide an index capable of evaluating resistance in a capillary.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing system, comprising: processing circuitry configured to
    acquire medical image data of a heart of a patient obtained from a medical scan of the patient performed with a medical imaging apparatus;
    determine, by fluid analysis of the medical image data, a blood-vessel blood flow index in a coronary artery of the patient and a myocardial blood flow index in a myocardial region of the patient to which the coronary artery supplies blood, the blood-vessel blood flow index being determined from the medical image data collected from the patient in a stressed state or a resting state, the myocardial blood flow index being determined from the medical image data collected from the patient in a same state as when the blood-vessel blood flow index is acquired;
    store, in a memory, first data that maps the myocardial blood flow index to a three-dimensional voxel space indicating the heart of the patient and second data that maps the blood-vessel blood flow index to a blood-vessel region in the three-dimensional voxel space;
    transform the acquired medical image data of the patient into an index indicating a resistance in capillaries of the patient that supply blood to the myocardial region, by extracting, from the memory, the first data and the second data, and obtaining the index by calculating a ratio of the blood-vessel blood flow index and the myocardial blood flow index based on the extracted first data and the extracted second data; and
    cause a display to display the obtained index indicating the resistance in the capillaries of the patient that supply blood to the myocardial region.

2. The medical information processing system according to claim 1, wherein the processing circuitry is further configured to calculate the index, which indicates a force of a blood vessel to send the blood to the myocardial region and diffusion of the blood in the myocardial region.

3. The medical information processing system according to claim 1, wherein the processing circuitry is further configured to:
    acquire a plurality of blood-vessel blood flow indices in a plurality of coronary arteries and a single myocardial blood flow index in which a plurality of myocardial blood flow indices in a plurality of myocardial regions to which the respective coronary arteries supply blood are combined, and
    obtain the index by calculating a ratio of the plurality of blood-vessel blood flow indices and the single myocardial blood flow index.

4. The medical information processing system according to claim 1, wherein the processing circuitry is further configured to:
    acquire a first blood-vessel blood flow index in an end portion on an upstream side and a second blood-vessel blood flow index in an end portion on a downstream side of a certain range of a coronary artery that supplies blood to the myocardial region and a myocardial blood flow index in the myocardial region, and
    obtain the index by calculating a ratio of a difference between the first blood-vessel blood flow index in the end portion on the upstream side and the second blood-vessel blood flow index in the end portion on the downstream side and the myocardial blood flow index in the myocardial region.

5. The medical information processing system according to claim 1, wherein the processing circuitry is further configured to:
    divide the coronary artery and the myocardial region to which the coronary artery supplies blood into a plurality of ranges,
    acquire, for each of the divided ranges, a first blood-vessel blood flow index in an end portion on an upstream side and a second blood-vessel blood flow index in an end portion on a downstream side of each of the ranges and local myocardial blood flow index in a myocardial region corresponding to each of the ranges, and
    obtain the index for each of the divided ranges by calculating a ratio of a difference between the first blood-vessel blood flow index in the end portion on the upstream side and the second blood-vessel blood flow index in the end portion on the downstream side and the local myocardial blood flow index in the myocardial region corresponding to each of the ranges.

6. The medical information processing system according to claim 1, wherein the processing circuitry is further configured to perform control of displaying a display image in which information on the calculated index is displayed on a medical image that includes at least one of the myocardial region and the coronary artery.

7. The medical information processing system according to claim 5, wherein the processing circuitry is further configured to perform control of displaying a color image in which the indices calculated for the respective divided ranges are represented in certain colors and allocated on a three-dimensional image of one of the myocardial region and the coronary artery.

8. The medical information processing system according to claim 5, wherein the processing circuitry is further configured to perform control of displaying a display image in which the coronary artery is represented on a two-dimensional plane along a long-axis direction and a graph that represents a change of the indices calculated for the respective ranges of the coronary artery such that positions in the display image and positions in the graph are associated with one another.

9. The medical information processing system according to claim 8, wherein the processing circuitry is further configured to perform control of displaying a result of myocardial perfusion on the display image.

10. The medical information processing system according to claim 5, wherein the processing circuitry is further configured to perform control of displaying a color image in which the coronary artery and the myocardial region are displayed in a distinguishable manner and the indices calculated for the respected divided regions are represented in certain colors on a display image in which a myocardium is displayed in polar coordinates.

11. The medical information processing system according to claim 5, wherein the processing circuitry is further configured to perform control of
    displaying at least two of a first color image in which the indices calculated for the respective divided ranges are represented in certain colors and allocated on a three-dimensional image of one of the myocardial region and the coronary artery, a combination of a display image in which the coronary artery is represented on a two-dimensional plane along a long-axis direction and a graph that represents a change of the indices calculated for the respective ranges of the coronary artery, and a second color image in which the coronary artery and the myocardial region are displayed in a distinguishable manner and the indices calculated for the respective divided ranges are represented in certain colors on a display image in which a myocardium is displayed in polar coordinates, and arranging and displaying markers indicating an approximately identical position on at least the displayed two of the first color image, the combination of the display image and the graph, and the second color image.

12. The medical information processing system according to claim 11, wherein when the markers are displayed, the processing circuitry is further configured to perform control of further displaying a short-axis cross-sectional image of the coronary artery at the arranged position.

13. The medical information processing system according to claim 5, wherein the processing circuitry is further configured to perform control of further displaying, in a superimposed manner, a three-dimensional image of the coronary artery and a color image in which indices of the respective ranges are represented in certain colors on a three-dimensional image of the myocardial region, and further displaying a marker indicating a position in the coronary artery and a fractional flow reserve at a position of the marker.

14. The medical information processing system according to claim 5, wherein the processing circuitry is further configured to perform control of displaying a three-dimensional image of the coronary artery, a marker indicating a position in the coronary artery, the index at a position of the marker, and a fractional flow reserve at the position of the marker.

15. The medical information processing system according to claim 5, wherein the processing circuitry is further configured to perform control of displaying a result of myocardial perfusion on a display image in which a myocardium is displayed in polar coordinates, and displaying, in a distinguishable manner, a region in which the index is smaller than a threshold in the myocardial region included in the display image.

16. The medical information processing system according to claim 5, wherein the processing circuitry is further configured to perform control of displaying a result of myocardial perfusion on a three-dimensional image of a myocardium, and displaying, in a distinguishable manner, a region in which the index is smaller than a threshold in the myocardial region included in the three-dimensional image.

17. The medical information processing system according to claim 5, wherein the processing circuitry is further configured to perform control of displaying a three-dimensional image of the coronary artery, and when receiving a designation operation of designating a position in the coronary artery in the three-dimensional image, perform control of displaying, side by side, a fractional flow reserve at the received position, a result of myocardial perfusion in a myocardial region to which the coronary artery at the received position supplies blood, the index at the received position, and a value based on a pixel value at the received position.

18. The medical information processing system according to claim 5, wherein the processing circuitry is further configured to perform control of displaying a three-dimensional image of a myocardium, and when receiving designation operation of designating a myocardial region in the three-dimensional image, perform control of displaying, side by side, a fractional flow reserve in a particular coronary artery that supplies blood to the received myocardial region, a result of myocardial perfusion in the received myocardial region, and the index in the received myocardial region.

19. The medical information processing system according to claim 17, wherein the processing circuitry is further configured to perform control of displaying a recommended therapeutic strategy for at least one of the received position and the received myocardial region, based on a result of comparison between each of display items that are displayed side by side and a threshold that is set for each of the display items.

20. A medical information processing method comprising:
acquiring medical image data of a heart of a patient obtained from a medical scan of the patient performed with a medical imaging apparatus;
determining, by fluid analysis of the medical image data, a blood-vessel blood flow index in a coronary artery of the patient and a myocardial blood flow index in a myocardial region of the patient to which the coronary artery supplies blood, the blood-vessel blood flow index being determined from the medical image data collected from the patient in a stressed state or a resting state, the myocardial blood flow index being determined from the medical image data collected from the patient in a same state as when the blood-vessel blood flow index is acquired;
storing, in a memory, first data that maps the myocardial blood flow index to a three-dimensional voxel space indicating the heart of the patient and second data that maps the blood-vessel blood flow index to a blood-vessel region in the three-dimensional voxel space;
transforming the acquired medical image data of the patient into an index indicating a resistance in capillaries of the patient that supply blood to the myocardial region, by extracting, from the memory, the first data and the second data, and obtaining the index by calculating a ratio of the blood-vessel blood flow index and the myocardial blood flow index based on the extracted first data and the extracted second data; and
displaying the obtained index indicating the resistance in the capillaries of the patient that supply blood to the myocardial region.

21. A medical information processing system, comprising:
processing circuitry configured to
acquire medical image data of a heart of a patient obtained from a medical scan of the patient performed with a medical imaging apparatus;
transform the acquired medical image data of the patient into an index indicating a resistance in capillaries of the patient that supply blood to the myocardial region, by acquiring, from the medical image data, a blood-vessel blood flow index in a coronary artery of the patient and a myocardial blood flow index in a myocardial region of the patient to which the coronary artery supplies blood, and obtaining the index by calculating a ratio of the blood-vessel blood flow index and the myocardial blood flow index, the blood-vessel blood flow index being acquired from the medical image data collected from the patient in a stressed state or a resting state, the myocardial blood flow index being acquired from the medical image data collected from the patient in a same state as when the blood-vessel blood flow index is acquired; and cause a display to display an image that maps a spatial distribution of the obtained index indicating the resistance in the capillaries of the patient that supply blood to the myocardial region onto a three-dimensional cardiac image, and to display a region, in which a value of the obtained index is lower than a threshold, in a distinguishable manner from other regions in the three-dimensional cardiac image.

22. A medical information processing system, comprising:

processing circuitry configured to read, from a memory, three-dimensional medical image data of a heart of a patient obtained from a medical scan of the patient performed with a medical imaging apparatus;

divide a coronary artery region of the three-dimensional medical image data into a plurality of blood-vessel segments;

identify, for each blood-vessel segment, a myocardial segment supplied with blood by that blood-vessel segment based on positional information of the blood-vessel segment in the three-dimensional medical image data;

determine, for each blood-vessel segment, a blood-vessel blood flow index in a blood-vessel segment from the three-dimensional medical image data, the blood-vessel blood flow index being acquired from the three-dimensional medical image data collected from the patient in a stressed state or a resting state, determine, for each myocardial segment, a myocardial blood flow index in a myocardial segment to which the corresponding blood-vessel segment supplies blood from the three-dimensional medical image data, the myocardial blood flow index being determined from the three-dimensional medical image data collected from the patient in a same state as when the blood-vessel blood flow index is determined; and calculate an index indicating a resistance in capillaries of the patient that supply blood to the myocardial segment based on the blood-vessel blood flow index in a blood-vessel segment and the corresponding myocardial blood flow index in a myocardial segment.

* * * * *